(12) United States Patent
Yee et al.

(10) Patent No.: US 7,008,415 B2
(45) Date of Patent: Mar. 7, 2006

(54) GENERATING SCANNING SPOT LOCATIONS FOR LASER EYE SURGERY

(75) Inventors: Kingman Yee, Sunnyvale, CA (US);
Erik Gross, San Jose, CA (US)

(73) Assignee: Visx, Inc., Santa Clara, CA (US)

( * ) Notice: Subject to any disclaimer, the term of this patent is extended or adjusted under 35 U.S.C. 154(b) by 135 days.

(21) Appl. No.: 10/655,151

(22) Filed: Sep. 3, 2003

(65) Prior Publication Data

US 2004/0059398 A1 Mar. 25, 2004

Related U.S. Application Data

(62) Division of application No. 09/805,737, filed on Mar. 13, 2001, now Pat. No. 6,673,062.

(60) Provisional application No. 60/189,633, filed on Mar. 14, 2000.

(51) Int. Cl.
*A61B 18/18* (2006.01)

(52) U.S. Cl. ............... 606/5; 606/4; 606/10; 351/211; 351/212; 128/898

(58) Field of Classification Search ............... 606/4–6, 606/8–11; 351/211–216; 128/898
See application file for complete search history.

(56) References Cited

U.S. PATENT DOCUMENTS

| 5,163,934 | A |  | 11/1992 | Munnerlyn |
| 5,683,379 | A |  | 11/1997 | Hohla |
| 5,740,815 | A |  | 4/1998 | Alpins |
| 5,871,018 | A | * | 2/1999 | Delp et al. ............... 128/898 |
| 5,903,458 | A | * | 5/1999 | Stewart et al. ............ 700/98 |
| 6,010,497 | A |  | 1/2000 | Tang et al. |
| 6,063,028 | A |  | 5/2000 | Luciano |
| 6,129,722 | A |  | 10/2000 | Ruiz |
| 6,203,539 | B1 |  | 3/2001 | Shimmick et al. |
| 6,245,059 | B1 | * | 6/2001 | Clapham ................... 606/5 |
| 6,299,307 | B1 |  | 10/2001 | Oltean et al. |
| 6,413,251 | B1 |  | 7/2002 | Williams |
| 6,599,285 | B1 | * | 7/2003 | Lieberman et al. ......... 606/5 |

* cited by examiner

*Primary Examiner*—A. Farah
(74) *Attorney, Agent, or Firm*—Townsend and Townsend and Crew LLP

(57) ABSTRACT

Scanning spot locations are generated for ablating tissue using a scanning laser beam over a treatment region by taking a target function representing a desired lens profile of ablation with a basis function representing a treatment profile produced by overlapping scanning spots in a particular treatment pattern. In some embodiments, the basis function is a two-dimensional function representing a two-dimensional section of a three-dimensional treatment profile, which has symmetry with respect to the two-dimensional section extending along the treatment pattern. For example, the treatment pattern is generally straight for myopic and hyperopic cylinders, and is generally circular for myopia and hyperopia. The fit produces ablation depths for discrete scanning spots, which are used to calculate the number of pulses at each reference position along the two-dimensional section. The pulses are distributed along the treatment pattern to produce the desired overlapping effect.

26 Claims, 11 Drawing Sheets

GENERATING SCANNING SPOT LOCATIONS FOR LASER EYE SURGERY

This application is a divisional of U.S. patent application Ser. No. 09/805,737, filed Mar. 13, 2001 now U.S. Pat. No. 6,673,062, which is based on and claims the benefit of U.S. Provisional Patent Application No. 60/189,633, filed Mar. 14, 2000, the entire disclosures of which are incorporated herein by reference.

BACKGROUND OF THE INVENTION

The present invention relates generally to tissue removal techniques and, more particularly, to generating locations for scanning with a laser to achieve a desired ablation profile for correction of errors in vision during laser eye surgery.

A scanning system has the ability to trace out an arbitrary pattern with a small low energy spot. In most cases, a small spot equates to finer scanning details but at the expense of requiring more pulses to remove a given volume. The notion that a small spot will give a better fit than a large spot is generally true for arbitrary spot and ablation shapes, but the spot shapes can also affect the fit. For instance, trying to fit round disks into a square shape will result in a residue. The emphasis on getting a good fit should be on choosing a good balance of spot geometry and size.

Small spot scanners have their problems. A small spot will have smaller coverage per shot, thereby requiring more pulses to remove a given ablation volume (inversely proportion to the area of the spot size). A larger spot will require a substantially smaller number of pulses but at the expense of resolution. Understanding how treatment varies with spot overlap will ease our ability to create ablation patterns.

Present ablation algorithms follow a removal or subtractive process. An ablation spot is placed on a location along the two-dimensional corneal surface. This spot ablates a volume of tissue from the surface to produce a crater on this surface. Another spot is applied at another location along the two-dimensional corneal surface and another crater is produced. The challenge lies in placing the craters in the correct locations such that adding up the overlapping craters will produce the desired surface without producing undesirable residues and requiring excessive processing time.

SUMMARY OF THE INVENTION

The present invention relates to tissue ablation utilized in, for instance, corneal sculpting. In general, embodiments of the invention determine a treatment table containing scanning spot locations and characteristics (e.g., size, shape, and depth) for directing overlapping scanning spots of a laser beam to achieve a target ablation profile. Some embodiments of the invention use symmetry effects (e.g., axisymmetry or bilateral symmetry) to simplify the overlap analysis to determine scanning spot locations for directing the laser beam to achieve a desired ablation profile. In specific embodiments, the spot center locations define a series of linear overlapping ablation paths, with the shape of the ablation paths preferably being selected in response to a desired change in an optical characteristic of the eye. The scanning spots can be uniform or variable in size, shape, and/or depth. Advantageously, these paths can produce ablation treatment profile elements which can be combined, adjusted, and positioned over the two-dimensional corneal surface to, in combination, produce the desire three-dimensional sculpting. The ablation profiles of the overlapping paths can be represented by basis functions, which may include an array of ablation profile data or can be expressed analytically for certain profiles.

An aspect of the present invention is directed to a method of generating a treatment table for ablating tissue using a scanning laser beam for generating scanning spots over a treatment region larger in area than the scanning spots. The method comprises providing a target function or lens function representing a desired lens profile for ablating the tissue by scanning spots of the laser beam on the tissue. A basis function represents a treatment profile produced by the overlapping scanning spots in a treatment pattern. The target function is fitted with the basis function to obtain the treatment table including scanning spot locations and characteristics for the overlapping scanning spots of the laser beam. In a specific embodiment, the scanning spot locations are randomized to produce a random scanning order. The scanning spot characteristics of a scanning spot may include scanning spot size, shape, and depth of the scanning spot at a specific scanning spot location.

Any desirable treatment pattern for scanning with overlapping scanning spots of the laser beam may be specified. In some embodiments, the overlapping scanning spots define a treatment pattern in the form of, e.g., a linear path, and the basis function is a two-dimensional function representing a two-dimensional section of a three-dimensional treatment profile which has symmetry with respect to the two-dimensional section extending along the treatment pattern. For example, the treatment pattern is generally straight for myopic and hyperopic cylinders, and is generally circular for myopia and hyperopia. In a specific embodiment, the lens function represents an ablation depth as a function of a distance from an optical axis of a cornea. The basis functions of a series of offset patterns are combined, the profiles of laterally adjacent paths often overlapping to provide a smooth treated surface.

In some embodiments, the spot size and shape are generally fixed. In other embodiments, the spot size and shape are variable. The ability to achieve the desired ablation profile using fixed spot size and/or shape may allow the use of a more simplistic laser source and simplify the ablation process.

In specific embodiments, fitting the lens function with the basis function includes fitting at N discrete evaluation points. The basis function includes M discrete basis functions representing M overlapping scanning spots. The M discrete basis functions may represent M overlapping scanning spots across a treatment zone length representing the length across a generally two-dimensional section which is oriented normal across a generally straight treatment pattern or which is oriented radially across a generally circular treatment pattern.

For a treatment profile having a generally uniform two-dimensional section oriented normal across a generally straight treatment pattern, the discrete basis functions represent the two-dimensional section as $$X_i(x_j) = y_i(x_j) = \sqrt{(s/2)^2 - (x_j - x_{0i})^2}; \text{ or,}$$

for a treatment profile having a generally uniform two-dimensional section oriented radially across a generally circular treatment pattern, the discrete basis functions represent the two-dimensional section as $$X_i(x_j) = \theta_i(x_j) = \cos^{-1}\left(\frac{x_j^2 + x_{0i}^2 - (s/2)^2}{2 \cdot x_{0i} \cdot x_j}\right)$$

where
s is the diameter of the scanning spot;
j=1, ..., N;
$x_j$ is a reference x-coordinate for the two-dimensional section measured from an optical axis of the cornea of a $j^{th}$ evaluation point for the center of the scanning spot;
$x_{0i}$ is an x-coordinate for a center of an $i^{th}$ scanning spot; $(x_{0i}-s/2) \leq x_j \leq (x_{0i}+s/2)$;
$y_i(x_j)$ is a depth of the $i^{th}$ basis function for the generally straight treatment pattern; and
$\theta_i(x_j)$ is a coverage angle of the $i^{th}$ basis function for the generally circular treatment pattern.

In a specific embodiment, fitting the lens function with the basis function comprises solving the following equation for coefficients $a_i$ representing treatment depth for the $i^{th}$ scanning spot:

$$f(x_j) = \sum_{i=1}^{M} a_i X_i(x_j)$$

where
$f(x_j)$ is the lens function; and
i=1, ..., M.

Fitting the lens function and the basis function may include specifying a deviation for each of the N discrete evaluation points. The method may include refitting the lens function with the basis function by varying the deviations to iterate for an acceptable fit or a best fit. The method may further include refitting the lens function with the basis function by varying the number of scanning spots M to iterate for a best fit. The method may also include refitting the lens function with the basis function by varying the size of the scanning spot and/or the number of scanning pulses at a scanning spot location to iterate for a best fit. A merit function may be defined to represent an error of fit between the lens function and the basis function. The method includes minimizing the merit function to achieve the best fit. In some embodiments, the merit function and the total number of scanning spots in the treatment table are both minimized to achieve the best fit with the least number of scanning spots.

Another aspect of the invention is directed to a method of generating scanning spot locations for ablating tissue using a scanning laser beam for generating scanning spots over a treatment region larger in area than the scanning spots. The method comprises providing a lens function representing a desired lens profile for ablating the tissue by scanning spots of the laser beam on the tissue. A basis function represents a treatment profile produced by the overlapping scanning spots along a treatment path. The basis function represents a section oriented across the treatment path. The lens function is fitted with the basis function to obtain the scanning spot locations for the overlapping scanning spots of the laser beam. In specific embodiments, the treatment profile is symmetrical with respect to an axis of symmetry.

In accordance with another aspect of the invention, a method for fitting a three-dimensional target profile comprises providing a two-dimensional basis function including overlapping portions to represent a three-dimensional profile which has symmetry with respect to a two-dimensional section extending along a treatment pattern. The three-dimensional target profile is fitted with the two-dimensional basis function to obtain a distribution of the overlapping portions.

In accordance with yet another aspect of the present invention, a system for ablating tissue comprises a laser for generating a laser beam, and a delivery device for delivering the laser beam to a tissue. A controller is configured to control the laser and the delivery device. A memory is coupled to the controller, and comprises a computer-readable medium having a computer-readable program embodied therein for directing operation of the system. The computer-readable program includes a first set of instructions for generating a treatment table for ablating the tissue over a treatment region larger in area than the spot size of the laser beam to achieve a desired lens profile for ablating the tissue, a second set of instructions for controlling the laser to generate the laser beam, and a third set of instructions for controlling the delivery device to deliver the laser beam to the tissue at the scanning spot locations.

In specific embodiments, the first set of instructions includes a first subset of instructions for providing a target function representing the desired lens profile for ablating the tissue by scanning spots of the laser beam on the tissue, a second subset of instructions for providing a basis function representing a treatment profile produced by the overlapping scanning spots in a treatment pattern, and a third subset of instructions for fitting the target function with the basis function to obtain the treatment table including scanning spot locations and characteristics for the overlapping scanning spots of the laser beam.

DESCRIPTION OF THE SPECIFIC EMBODIMENTS

I. GENERATION OF SCANNING LOCATIONS AND DEPTHS

A. Treatment Space

Treatment space or profile is the treated form (or profile) created by a given spatial pulse sequence taking into account its overlap characteristics.

1. Rectangular Spot Shape in Straight Pattern

As an introductory example, a simple square spot with a treatment intensity of approximately 0.25 μm per pulse is used. The overlap is set to 33%. A 1 mm square spot centered at position (in mm) [0, 0] will have the next spot at [0, 0.33]. The area the two pulses have in common is 0.67 mm². The offset (step size) from the first pulse is 0.33 mm. Continuing this sequence for a total of N pulses will produce a treated path of width 1 mm, and length 0.33*N mm. The overlap is 33% so the last pulse to coincide with the first pulse is the third pulse. The fourth pulse's edge is immediately adjacent to the first pulse. Assuming that the positioning is perfect, they will share a common edge. Looking in from a meridian cross section, the slope is (depth per pulse)/0.33 mm. All positions after the third pulse will have a depth of (3*depth per pulse). The slope also occurs at the trailing end. The cut profile from the ends has the box shape, with a depth of (3*depth per pulse) and a width of 1 mm. The slope is:

$$Slope = \frac{depth\ per\ pulse}{step\ size}.$$

Figure 1:
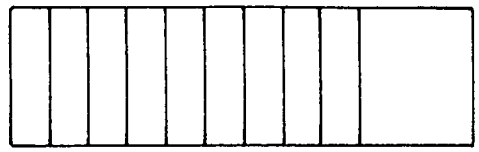
FIG. 1 is a top projection of a set of overlapping square pulses illustrating a straight pattern.
Figure 2:
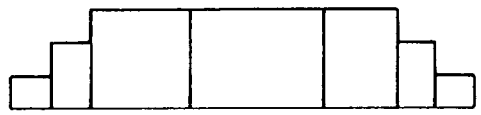
FIG. 2 is a cross sectional projection of the overlapping square pulses of FIG. 1 along the central meridian illustrating the cross-sectional treatment profile.

The treatment profile of FIGS. 1 and 2 is generated by scanning overlapping square spots in a straight treatment pattern. As shown in FIG. 1, the shape of the trench is rectangular in shape. The stacking of pulses has the first interval with a single pulse depth, the second interval with a double pulse depth, and the third interval with a triple pulse depth, as seen in FIG. 2. The depth of the trench remains the same after the third pulse because the overlap is ⅓ of the spot, i.e., the fourth pulse does not overlap the first.

The treatment profile generated by overlapping rectangular spots is relatively simplistic and easy to represent mathematically due to the rectangular spot shape as well as the straight-line pattern. The complexity of the mathematical representation increases for round spots, particularly if the spots overlap in a nonlinear pattern.

2. Round Spot Shape in Straight Pattern

Figure 3:
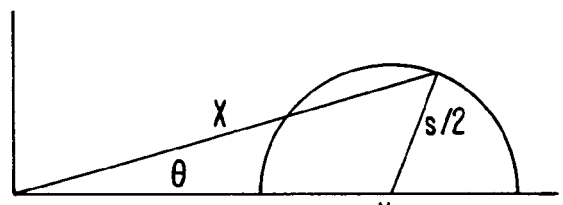
FIG. 3 shows a top projection of a treatment profile of a round spot trench.

FIG. 3 shows a round spot having a diameter or spot size of s. x is a spatial coordinate from the origin to a point on the trench produced by the round spot (which may be discrete). $x_0$ is the position of a basis function or the center of the ablation trench produced by the round spot, and θ is the coverage angle. A basis function is a mathematical representation of the treatment profile produced, for instance, by overlapping scanning spots in a specified treatment pattern. Here, each round spot is assumed to produce an ablation with a uniform ablation depth. Adjustments may be made for nonuniform energy distribution profiles, "central islands," and other local ablation depth variations, and the like.

Overlapping a round spot produces similar characteristics as overlapping a rectangular spot. Repeating the same exercise for overlapping the round spot in a straight pattern as done with the square spot, the side profile will have the same look as the square spot. The leading and trailing slopes will have the same slopes as those of the square spot. The profiles along the ends are different. It is semicircular in shape, or more precisely, semi-elliptical in shape, with a maximum depth of $$Depth_{max} = \frac{spot\ size}{step\ size} \cdot depth\ per\ pulse.$$

The slope is the same as described in the square spot. The round spot has a different edge pattern. Without a better descriptive phrase to describe it, it has a "cloud" effect to its edge.

The basis function for a round spot in a straight pattern is:

$$y_i(x) = \sqrt{(spotsize/2)^2 - (x - x_{0i})^2}$$

with $$(x_{0i} - spot\ size/2) < x < (x_{0i} + spot\ size/2);$$

where i is the running index of the basis functions;

$x_{0i}$ is the position of the $i^{th}$ basis function (i.e., the center of the $i^{th}$ spot) measured from the origin;

$y_i(x)$ is the trench depth of the $i^{th}$ basis function; and x is the spatial coordinate from the origin (e.g., optical axis of a cornea) to a point on the trench.

Fitting the function in a computer algorithm requires the coordinate system to be discrete. Defining j as the running index for the x spatial dimension, the trench depth is the same as above but with x replaced by $x_j$, $$y_i(x_j) = \sqrt{(spotsize/2)^2 - (x_j - x_{0i})^2}$$

where j is the running index for the sampling or evaluation points.

3. Round Spot Shape in Ring Pattern

Figure 4A:
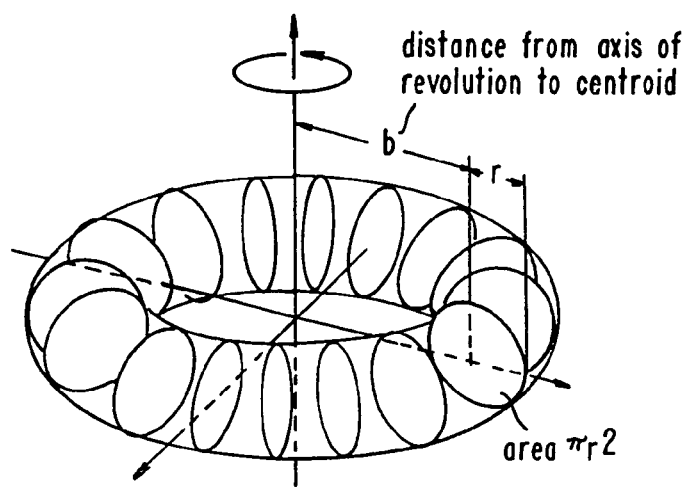
FIG. 4a is a schematic view of a circle rotated about the z-axis.

Generation of a ring treatment pattern makes use of axisymmetry. To illustrate how symmetry affects the overlap, consider a circular disk of radius r with its center b' away from the origin as depicted in FIG. 4a. Recall from differential geometry that its normal vector (right-hand rule) gives the "direction of the surface". The disk's direction vector at anytime is in the x-y plane thus implying that the surface of the disk itself lies in the y-z plane. Revolving this disk about the origin in the direction of its normal vector (z-axis) will generate a bagel shaped volume. The bagel will have a radius of b' and a thickness of 2r. This assumes that b'>r.

Consider again, the same disk but only the top half (z>0). The bottom is cut off at the x-y plane. Rotating this half disk about the surface along its normal vector will generate a semi "flat bottom sliced bagel" ring with a diameter of 2b' and thickness of r. Integrating the volume as the half disk moves about the origin will produce the volume of the flat bottom bagel. This type of "differential volume" will allow us to produce a "bowl" shape (flat on one side, curved on the other) similar to the bottom half of a sliced bagel.

Figure 4B:
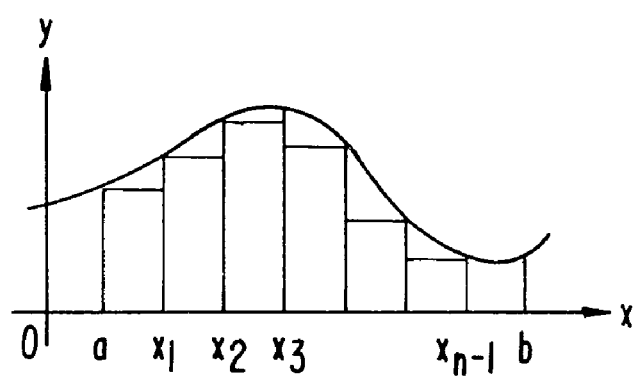
FIG. 4b shows a cross-sectional projection of an arbitrary shape.

One method for calculating volume is a 3-D version of Simpson's rule. FIG. 4b shows a cross section of a set of circular rings at a, $x_1, \ldots, x_{(n-1)}$ with a constant thickness of $\Delta x$. The top curve is the desired target shape representing, for example, a lens volume. The columns are cross sections of "thick" rings, spaced $x_j$ apart. Summing a particular set of rings will produce the desired volume. Note that this is mathematically easy to do because the basis functions are orthogonal. The rings following Simpson's rule will need to be very thin to get a good approximation to the curve (i.e. the error is on the order of $\theta^2(x)$).

Generalizing these approaches, symmetric objects can be generated in a "space" minus one dimension. For example, a symmetric 3-D object can be generated in 2-D space if symmetry is utilized. Generating these basis "rings" or treatment volumes from differently sized circular spots is the basis for one aspect of the present invention.

The thin lens volume is generated using flat bottom bagel shaped rings. Finding the different combinations of ring radii (b') and thickness (r) to generate the lens is done via, for example, a linear least square fitting routine.

Scanning a continuous circular spot in a large ring pattern will produce a result that resembles a bagel with a half-circular cross section (like a sliced bagel). As the ring's position gets closer to the origin, the ring's cross section becomes very noncircular because the ablation spot overlap characteristics change as the ring's radius changes.

Figure 4C:
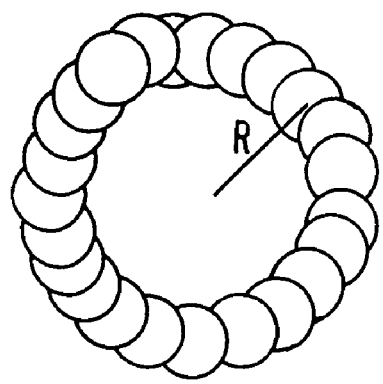
FIG. 4c is a top projection of a set of overlapping circular pulses illustrating a ring pattern.

The scan pattern for a round spot in a ring pattern will look somewhat like a torus but with a radial dependence resulting in a bulge toward the origin. To understand this radial dependence, consider a spot moving along a ring as shown in FIG. 4c. The outer portion of the spot will have an angularly smaller coverage than that of the inner portion. That is, the overlap for the outer portion of the spot is less than the inner portion. The functional expression for the arc length for this spot as a function of the radial distance is an arccosine:

$$\theta_i(x) = \cos^{-1}\left(\frac{x^2 + x_{0i}^2 - (s/2)^2}{2 \cdot x_{0i} \cdot x}\right)$$

or in terms of spot size or diameter, $$\theta_i(x) = \cos^{-1}\left(\frac{x^2 + x_{0i}^2 - (\text{spot size}/2)^2}{2 \cdot x_{0i} \cdot x}\right)$$

where
  i is the running index of the basis functions;
  x is the spatial coordinate from the origin (e.g., optical axis of a cornea) to a point on the trench; and
  $x_{0i}$ is the position of the $i^{th}$ basis function (i.e., the center of the $i^{th}$ spot) measured from the origin; and
  $\theta_i(x)$ is the coverage angle of the $i^{th}$ basis function.

FIG. 3 shows that the $i^{th}$ basis function is defined from $x_{0i}-s/2<x<x_{0i}+s/2$ and zero otherwise. x is continuous but actual implementation in an algorithm to solve for the scanning coordinates or locations will have discrete x.

A discrete coordinate system facilitates fitting the function in a computer algorithm. Defining j as the running index for the x spatial dimension, the angle of coverage is the same as above but with x replaced by $x_j$, $$\theta_i(x_j) = \cos^{-1}\left(\frac{x_j^2 + x_{0i}^2 - (\text{spot size}/2)^2}{2 \cdot x_{0i} \cdot x_j}\right)$$

where j is the running index for the sampling or evaluation points.

Figure 5:
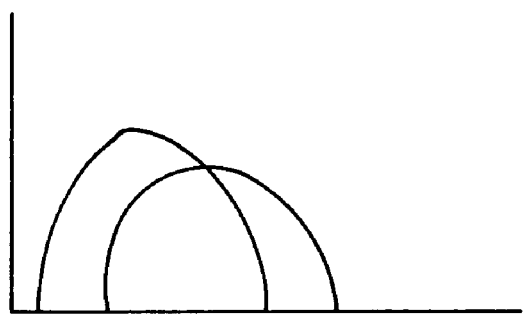
FIG. 5 shows the asymmetric treatment profiles of the overlapping circular pulses in the ring pattern of FIG. 6 taken along a radial section of the ring pattern.

A feature of these treatment "rings" is the asymmetric treatment space profile with respect to the radial direction from the origin as shown in FIG. 5. The profiles get more asymmetric as the pulse rings approach the origin, as illustrated by the increased asymmetry of profile A over profile B. This feature allows the fitting of a centrally maximum curved surface. The coefficient of each basis function will give the treatment depth.

4. Treatment Matrix

The above examples employ specific treatment profiles that can be expressed in analytical forms for achieving relatively simple types of target ablation profiles. Other treatment profiles may be used. A general treatment matrix includes data of treatment profiles produced by overlapping scanning spots of any desired shapes and sizes.

At one time it was thought that the laser-tissue interaction resulted in a flat ablation profile, so that each pulse could be thought of as removing a disc of material, with a diameter equal to the laser iris width and a uniform depth. Empirical evidence, however, has shown that the laser-tissue interaction may result in a rather complicated ablation profile with a complex shape and characteristics that can vary significantly with the laser iris diameter. In general, the ablation profiles for different laser spot sizes can be digitized and arranged as a treatment matrix of ablation data to be used for numerically determining a treatment plan or table (i.e., ablation amplitudes for a treatment pattern of scanning spots) to achieve a target ablation profile. There will be a different set of data for each treatment medium including, for example, polymethylmethacrylate (PMMA), calibration plastic, human cornea, porcine cornea, or the like.

B. Target Profile Fitting

Fitting the basis function to the target function representing the target ablation profile produces the scanning spot locations and ablation depths. In specific embodiments, the target function is represented by the lens equation as described below.

The target profile fitting involves solving for a set of coefficients for the following target profile fitting matrix equation:

$$f(x) = \sum_{i=1}^{M} a_i X_i(x)$$

F=AX with the solution as an inversion

A=X$^{-1}$F where $X_i(x)$ is the $i^{th}$ basis function;

f(x) is a particular target profile, which may be expressed as a lens equation or represented by a target matrix of data; and $a_i$ is the amplitude of the $i^{th}$ basis function.

F is the lens equation or target matrix, X are the basis functions, and A is the treatment plan or table containing the amplitudes for a particular treatment pattern (i.e., the scanning spot locations and characteristics such as size, shape, and depth). The fitting program calculates A such that the error ($\chi^2$'s) between F and X is a minimum.

Some of the examples discussed above employ analytical basis functions. For instance, the basis functions X are $y_i(x_j)$ for the straight pattern and $\theta_i(x_j)$ for the ring pattern. The straight pattern is applicable in myopic and hyperopic cylinders, while the ring pattern is applicable in myopia and hyperopia. For phototherapeutic keratectomy (PTK), the treatment profile is essentially a centrally flat hyperopia ablation since PTK is a flat ablation. Thus, the basis function $\theta_i(x_j)$ can be used for PTK (while the lens equation for PTK is a constant value). Of course, the basis function may be represented by a general treatment matrix instead of the analytical functions. Furthermore, the target profile f(x) may be expressed as a lens equation which has been developed for certain cases such as myopia and hyperopia. Other target ablation profiles (e.g., an elliptical profile, a toric profile, a wavefront profile, or an arbitrary profile) may be expressed more generally as a target matrix.

Figure 6:
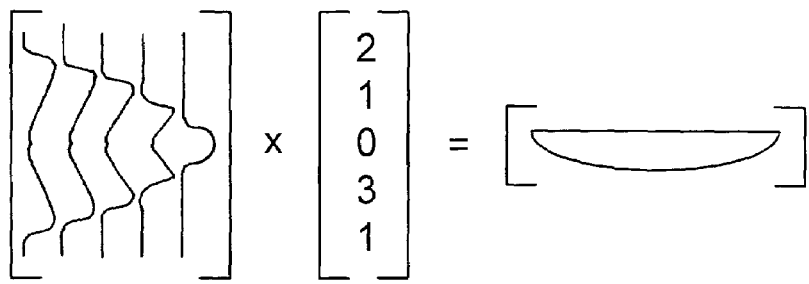
FIG. 6 is a one-dimensional, simplified representation of a target profile fitting equation.

FIG. 6 schematically illustrates in one dimensional simplified form the equation XA=F, where X is a basis function expressed in a general treatment matrix representing ablation profiles that may have relatively complex shapes, F is the target profile schematically shown as a lens, and A is the treatment plan or table to be solved. In this example, the treatment table is a pulse instruction vector (PIV) representing the laser instruction count for each basis function. In the specific example shown, the treatment matrix represents ablation profiles for five laser pulses (i.e., five particular laser pulse diameters or shapes at particular locations). The elements of the treatment table or PIV correspond to the numbers of pulses that can be combined to build an entire ablation having a shape that matches the target profile as close as possible. In that case, the elements of the treatment table or PIV are positive integers. The treatment table or PIV is used to operate the laser to achieve ablation that approximates the target profile. Note that a two-dimensional version of the equation (instead of the one-dimensional illustration shown in FIG. 6) will produce a three-dimensional model of the ablation profile.

1. Least Square Fitting Approach Using Analytical Lens Equations

The difficulty in performing the inversion of the target profile fitting equation to obtain A is that $X^{-1}$ is not orthogonal. One useful method for solving this equation is to use a least square fitting routine. An example of a suitable method for fitting the basis function is found in Numerical Recipes in C, $2^{nd}$ Ed., W. H. Press, S. A. Teukolsky, W. T. Vetterling, B. P. Flannery, Cambridge Univ. Press, pp. 671–675 (1992). The general model representation is $$f(x) = \sum_{i=1}^{M} a_i X_i(x)$$

where $X_1, \ldots, X_M$ are arbitrary functions of X, called basis functions, and M is the number of basis functions. The $X_i$'s need not be linear. The linearity is in respect to the linear dependence on the parameters $a_i$. The basis functions are the $y_i$'s for the straight treatment pattern or the $\theta_i$'s for the ring treatment pattern.

The merit function ($\chi^2$) is defined as $$\chi^2 = \left[ \frac{f(x_j) - \sum_{i=1}^{M} a_i X_i(x_j)}{\sigma_i} \right]^2$$

f(x) represents the target profile to be fitted with the basis functions. In specific embodiments, f(x) is the lens equation evaluated at $x_j$, that is, $f(x_j)$. The $\sigma_i$'s are the uncertainties or standard deviations of the $X_i$'s. These are typically set to one but can be altered if a more precise fit for certain parts of the curve is desired (e.g., the central half can be set to 0.25 and the outer half can be set to 1). For instance, decreasing the value of $\sigma_i$ for the central area and increasing it for the outlying area will force the fit to be more precise in the central region. The reduced $\chi^2$ is $$\chi_v^2 = \frac{\chi^2}{v}$$

where $v$ is the number of degrees of freedom.

To minimize $\chi^2$, the derivative of $\chi^2$ with respect to parameters $a_k$ for all M's is taken and set to zero.

$$0 = \sum_{i=1}^{M} \frac{1}{\sigma_i^2} \left[ f(x_j) - \sum_{i=1}^{M} a_i X_i(x_j) \right] X_k(x_j)$$

for i=1, ..., M. These are the normal equations of the least square problem. The two commonly used methods of obtaining the vector a is by LU decomposition and by Gauss-Jordon elimination. The Gauss-Jordon method will provide the variances of $a_i$ as part of the solution.

$\chi_v^2$ gives the relative "goodness" of fit. The better the fit, the closer $\chi_v^2$ approaches one ($\chi_v^2 \rightarrow +1$). If $\chi_v^2$ is less than one, it means the original estimates of $\sigma_i^2$'s are too large.

The input parameters used by the fitting routine are:

(1) The data generated by the lens equation, $f(x_j)$.

(2) The standard deviation $\sigma_i$ of each data point. Since the data is generated from the lens equation, the standard deviation is arbitrarily set to one. This arbitrariness needs to be addressed because the standard deviation affects $\chi^2$. Consistency is desired because once the values for the standard deviation is determined, it should not be changed if $\chi^2$ is to be used to determine the relative goodness of fit. A wide variety of fit evaluation methods could alternatively be used within the scope of the invention.

(3) The Basis Functions in Analytical Form.

2. Simulated Annealing Approach

Another computational technique that may be used for solving the target profile fitting equation is simulated annealing. Such a technique is described, for instance, in Numerical Recipes in C, $2^{nd}$ Ed., W. H. Press, S. A. Teukolsky, W. T. Vetterling, B. P. Flannery, Cambridge Univ. Press, pp. 444–451 (1992). Simulated annealing is an evolutionary optimization method using gradual, randomly induced changes to find the best solution to mathematically intractable problems.

Simulated annealing is a method used for minimizing (or maximizing) the parameters of a function. It is particularly suited to problems with very large, poorly behaved function spaces. Simulated annealing can be applied in the same way regardless of how many dimensions are present in the search space. It can be used to optimize any conditions that can be expressed numerically, and it does not require a derivative. It will not be fooled by local minima in the search space.

Simulated annealing is inspired by the observation that if a thermodynamic system is cooled slowly, it will end up very near its minimum energy state. For example, a piece of hot metal contains n molecules in rapidly changing orientations. If the metal is quenched in cold water the thermal energy rapidly leaves the metal and the molecules remain—"frozen forever"—in their last orientation. However, if the metal is allowed to cool gradually the molecules will continue changing orientation, but gradually favoring lower and lower energy states. Eventually all the molecules will be "frozen" into their lowest energy state. (In metals, the molecules align, forming crystals.) This is called annealing.

Instead of a piece of metal, the treatment table or pulse instruction vector (PIV) will be annealed. The PIV may be expressed as a 1 by N array of integers, each of which describes the number of pulses at a particular location and given pulse size, shape, and/or depth. The PIV may be expressed as follows:

$$\begin{bmatrix} \text{\# of 1 mm pulses at position 1} \\ \text{\# of 1 mm pulses at position 2} \\ \text{\# of 1 mm pulses at position 3} \\ \ldots \\ \text{\# of 6 mm pulses at position } M-1 \\ \text{\# of 6 mm pulses at position } M \end{bmatrix}$$

This vector can be very large. Some examples have upwards of 3000 elements.

To "simulate" annealing, two physical concepts are applied to solving the target profile fitting equation. The first is the concept of energy state to be minimized, which is analogous to the error or merit function ($\chi^2$) defined as $$\chi^2 = \sum_{i=1}^{M} [f(x_j) - a_i X_i]^2$$

where f(x) represents the target profile to be fitted with the basis functions $X_i$. In specific embodiments, f(x) is the target profile evaluated at $x_j$, that is, $f(x_j)$. The numerical value ($\chi^2$) to be minimized is the sum of the squares of the difference at each point between the target shape and the "test shape" or "working shape" during the iteration. This example employs a least square fit for minimizing the merit function.

The merit function may be modified to find a fit with more desirable optical qualities. For instance, a weighted merit function may be $$\chi^2 = \sum_{i=1}^{M} \left[ \frac{f(x_j) - a_i X_i}{\sigma_i} \right]^2$$

The $\sigma_i$'s are the uncertainties or standard deviations of the $X_i$'s. These are typically set to one but can be altered if a more precise fit for certain parts of the curve is desired (e.g., the central half can be set to 0.25 and the outer half can be set to 1). For instance, decreasing the value of $\sigma_i$ for the central area and increasing it for the outlying area will force the fit to be more precise in the central region.

The second physical concept that is applied in the fitting approach is that of temperature, which is analogous to a measure of the random change applied to the treatment table or PIV (i.e., change in the number of laser pulses) before each successive evaluation. In this case, each "degree" of "temperature" change will cause one random fluctuation in the PIV. For each fluctuation one element of the PIV will be randomly selected. That element will then be either incremented or decremented, again based on a random number. In the case that the element is already zero and a decrement is chosen, nothing will happen to that element, since only positive integers are acceptable. Evaluation of the "energy state" (i.e., merit function) takes place during the "temperature" change iteration for the PIV until a sufficiently low value for the merit function is achieved.

Figure 7:
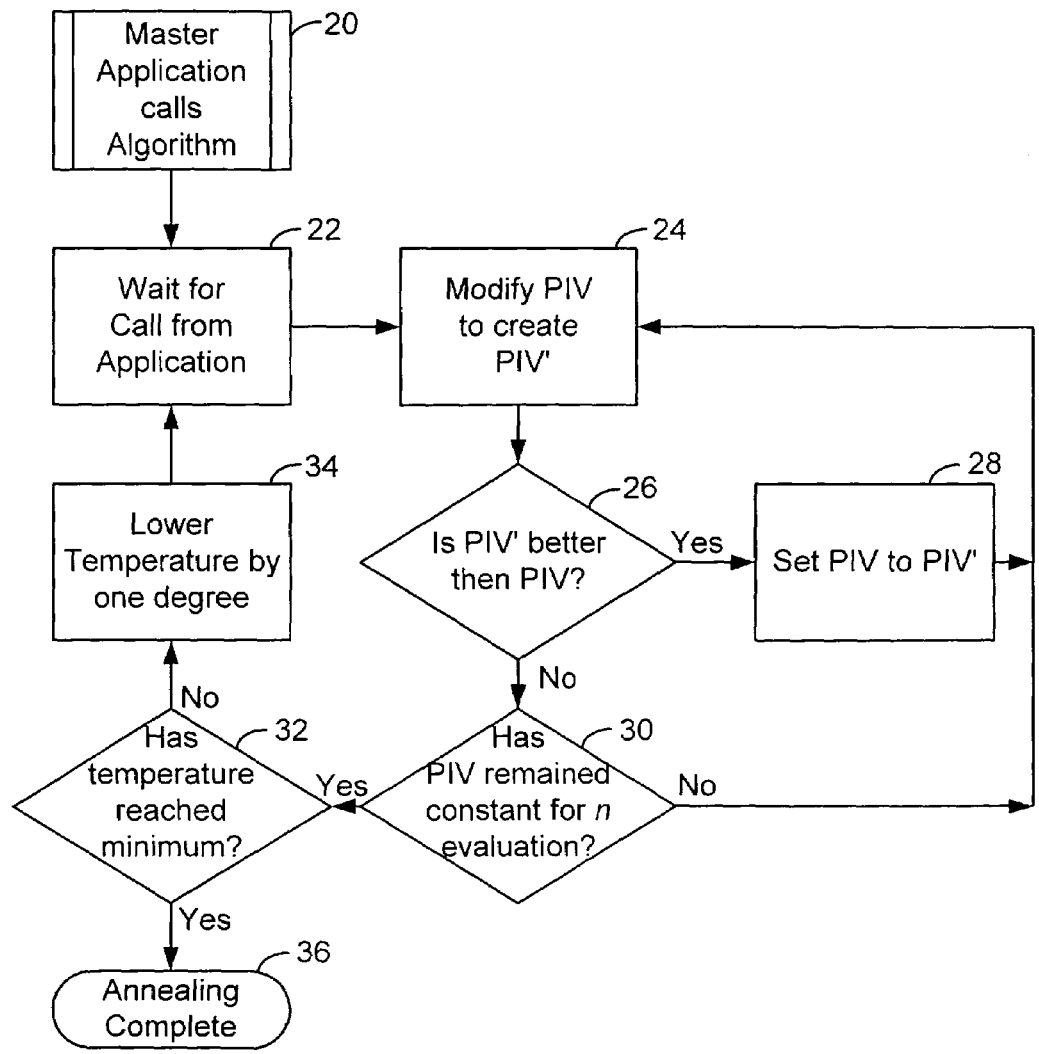
FIG. 7 is a flow diagram illustrating a simulated annealing method for solving a target profile fitting equation.

An example of implementing the simulated annealing procedure or algorithm is illustrated in FIG. 7. After the master application calls the algorithm (step 20) and the simulated annealing subroutine is initiated (step 22), the subroutine randomly modifies the treatment table or pulse interaction vector (PIV) according to the current temperature (i.e., size of the incremental change to an element of the PIV) to create the next vector PIV' (step 25). An evaluation takes place in step 26 to determine whether PIV' is better than PIV in reducing the merit function or "energy state." If PIV' is better than PIV, then the vector is updated by setting it to PIV' (step 28), and the iteration continues by following the loop back to step 24. If PIV' is not better than PIV, then the subroutine determines whether the vector has remained constant for a preset number (n) of evaluations (step 30). If not, the PIV is not updated and the iteration continues by returning to step 24. If n number of evaluations have taken place with no improvement of the PIV, then the subroutine determines in step 32 whether the temperature (i.e., the size of the incremental change) has reached a preset minimum value. If not, the temperature is lowered by one degree in step 34 (i.e., the size of the incremental change to an element of the PIV is lowered by a preset amount) and the iteration continues by returning to step 22. If the minimum temperature has been reached, then the annealing is complete (36) and the simulated annealing procedure is terminated. Therefore, the annealing process constitutes repeated evaluation of the PIV, at gradually decreasing temperatures. For a particular temperature the iteration cycle will repeat until a certain n number of evaluations have failed to show improvement. Once the solution meets some pre-determined "goodness of fit criteria" as represented by the merit function, the final solution is returned.

For problems with radial symmetry, such as spheres or round PTK's, the problem is solved in only one dimension.

For problems with bilateral symmetry, such as ellipses or cylinders, the problem becomes two dimensional. The method only needs to be used to solve one quarter of the surface and then the solution is applied over all four quadrants. This saves considerable computation. For problems with no symmetry, such as a wavefront map, the method solves for the entire surface.

Solving the target profile fitting equation numerically for a general two-dimensional surface, particularly without the benefit of symmetry, can be very difficult and can require a great deal of computational time. The simulated annealing approach can generally produce the best solution in a reasonable amount of time, preferably in real time.

The input parameters used by the simulated annealing routine are:

(1) The target profile data, which can represent any arbitrary shape. The target shape can be arbitrary, allowing for unlimited ablation possibilities, including the map from a wavefront type device or any other topography system. As long as the target profile can be described mathematically or with an array of data, the algorithm can use it. Radial or bilateral symmetry is not required, although the presence of symmetry can make the computation faster.

(2) The treatment matrix (i.e., basis function) which can represent any ablation sizes and shapes. The laser ablation shape does not have to be flat or smooth, or have specific shapes. As long as it can be measured and described mathematically or with an array of data, the simulated annealing process can be used. A unique description is provided for every unique pulse shape or size to be used. A fixed spot-size laser would have only one description, while a variable spot-laser could have as many as desired.

(3) The standard deviation $\sigma_i$ of each data point if a weighted merit function is used. It is noted that any merit function can be used. This allows the user to decide what aspect of the solution is most important. For example, extra "weighting" may be provided in the central portion of the lens, so that the algorithm will recognize that the center portion of the lens is the most important part and will sacrifice accuracy around the edges to get the best possible fit in the center portion. Moreover, the merit function is not limited to just the shape of the surface. For instance, the merit function can be linked to the number of pulses, so that the algorithm will favor solutions with fewer pulses. This helps to minimize the treatment time. In one example, the merit function is expressed as follows:

$$\chi^2 = \left\{ \sum_{i=1}^{M} \left[ \frac{f(x_j) - a_i X_i}{\sigma_i} \right]^2 \right\} \times \left( (N_{number\_of\_pulses})^2 + K_{offset} \right)$$

In this example, the merit function is just the surface fit function multiplied by the number of pulses squared plus a constant offset. The offset lets the user tune the relative importance of the surface fit versus the pulse count. If the offset is large compared to the number of pulses, then the merit function will be only mildly influenced by pulse count. The solution will tend to reduce the number of pulses, but only slightly. If the offset is comparable or small compared to the number of pulses then the merit function will be significantly influenced. The solution will compromise some goodness of fit in order to use fewer pulses. It is possible to have solutions with differing pulses because a variety of pulse sizes are used (e.g., a single five millimeter pulses can remove as much tissue as twenty five pulses of one millimeter diameter).

Other modification of the merit functions would include maximizing smoothness, (i.e. minimizing the first derivative of the surface error), meeting hardware constraints of the Laser delivery system (e.g., the Laser can only move so far in a given time), meeting biological constraints on the eye (e.g., pulses might be distributed over space and time to avoid excess thermal build up.)

C. Software Implementation Steps

1. Least Square Fitting Approach Using Analytical Lens Equations

The following steps are provided to illustrate an example of software implementation of the fitting approach of generating scanning locations and ablation depths using analytical lens equations.

Step 1. Evaluate Lens Equation. The lens equation is evaluated for N points (typically equally spaced) in the region $0 \leq x < L$ where L is the treatment zone radius for a ring pattern and is the treatment zone length for a straight pattern. N is set to about 300 in specific embodiments. If it is desired to emphasize the central portion of the lens equation (e.g., for myopia and myopic cylinder), a "shift" is subtracted from the treatment zone length.

For myopia and myopic cylinder, the lens equation is:

$$f(x_j) = \sqrt{R_1^2 - x_j^2} - \sqrt{\left(\frac{R_1(n-1)}{n-1+R_1 D}\right) - x_j^2} + C$$

where $0 \leq x_j \leq (L-\text{shift})$; and $j = 0, 1, \ldots, N-1$.

The constant C is defined as $$C = \sqrt{R_1^2 - s^2/4} + \sqrt{\left(\frac{R_1(n-1)}{n-1+R_1 D}\right) - \frac{s^2}{4}}$$

where $x_j$ is the reference x-coordinate measured from the optical axis of a cornea of the $j^{th}$ evaluation point for the center of the ablation or scanning spot;

s is the diameter of the ablation (i.e., spot size);

$R_1$ is the anterior radius of curvature of the cornea in meters;

$R_2$ is the final anterior radius of curvature of the cornea in meters;

n=1.377 is the index of refraction of the cornea;

D is the lens power of the ablation in diopters;

L is the treatment zone length representing the length across a generally uniform section which is oriented normal across a generally straight treatment pattern or is oriented radially across a generally circular treatment pattern; and shift is the amount of emphasis shift (shift typically is about 0–0.2, and can be set to zero).

Note that the above lens equation applies for the full range of angles in myopia to provide an axisymmetric profile, but applies only at a particular angle in myopic cylinder to provide a constant profile along a straight pattern.

For hyperopia and hyperopic cylinder, the lens equation is:

$$f'(x_j) = R_1 - \frac{R_1(n-1)}{n-1+R_1D} - \sqrt{R_1^2 - x_j^2} + \sqrt{\left(\frac{R_1(n-1)}{n-1+R_1D}\right) - x_j^2}$$

where $0 \leq x_j \leq (L\text{-shift})$; and j=0, 1, ..., N−1.

Note also that this lens equation applies for all angles in hyperopia and at a particular angle in hyperopic cylinder. A more detailed description of the lens equation is provided in Charles R. Munnerlyn et al., "Photorefractive Keratectomy: A Technique for Laser Refractive Surgery," *J. Cataract Refract. Surg.* (January 1988), which is incorporated herein by reference in its entirety.

For PTK, the lens equation is:

$$f''(x_j) = d$$

where d is a constant depth.

Step 2. Define basis rings at different radial positions for a ring pattern or define basis strips at different lateral positions for a straight pattern. A set of radial positions for basis rings or a set of lateral positions for basis strips are defined at $x_{0i}$. In specific embodiments, the number of rings/strips, M, may vary from about 17 to about 57. The positions of the ring/strip's radial center are equally spaced points in the region $0 \leq x \leq (L-\text{spot size}/2+\text{extended zone})$. The extended zone is for the taper or "feathering" of the outer circumference or edge. The extended zone typically ranges from about 0.1–0.5 mm, and may be fixed at about 0.2 mm. The extended zone also helps in the fitting routine. M is the number of basis functions. The number should be large enough to give a smooth fit and not too large to create quantized errors. Typically, M is about 7–97. In specific embodiments, M starts at about 17 for −1.5D or less, becomes about 27 between −1.5 and −2.5 D, and reaches about 47 for greater than −2.5 D. The $i^{th}$ basis function is $$x_{0i} = [(\text{treatment zone length}-\text{spot size}+\text{extended zone})/M]*i$$

wherein i=1, 2, ..., M.

Step 3. Define the positions for lens equation evaluations. N is the number of evaluation points. The $i^{th}$ position for lens equation evaluation is $$x_j = [\text{treatment zone length}-\text{shift}]/N]*j$$

where j=0, 1, ..., N−1.

Step 4. Assign a deviation, $\sigma_j$, for each $x_j$. The deviations will determine how tight the fit will be for each point. In a specific embodiment, the deviations are set to about 0.25 for the first 200 points as 0.25 and about 1.0 for the final 100 points. The deviation can be changed and optimized for different profiles and patterns.

Step 5. Apply least square fit. The function to fit the basis functions to the lens equation (i.e., fit $X(x_j)$ to $j(x_j)$) is $$f(x_j) = \sum_{i=1}^{M} a_i X_i(x_j)$$

where, for a ring pattern (myopia, hyperopia, and PTK), $$X_i(x_j) = \theta_i(x_j) = \cos^{-1}\left(\frac{x_j^2 + x_{0i}^2 - (\text{spot size}/2)^2}{2 \cdot x_{0i} \cdot x_j}\right)$$

and, for a straight pattern (myopic cylinder and hyperopic cylinder), $$X_i(x_j) = y_i(x_j) = \sqrt{(\text{spotsize}/2)^2 - (x_j - x_{0i})^2}$$

Note that $\cos^{-1}$ is valid only in the range $(x_{0i}-\text{spot size}/2) \leq x_j \leq (x_{0i}+\text{spot size}/2)$ for the ring pattern. The index j is the running index for evaluation and fitting points. The index i is the running index for the number of basis rings or basis strips.

The least square fit routine is an object that receives $x_j$ coordinates, the lens equation evaluated at these coordinates ($f(x_j)$ values), the basis functions $X_i(x_j)$, and returns a row (or column) matrix A representing the coefficients, and a $\chi^2$. Once again, a variety of fit or optimization routines might alternatively be employed.

Step 6. Evaluate closeness of fit. $\chi^2$ is recalculated if necessary, that is, if any changes are made to the returned matrix A. $\chi^2$ will give the goodness of fit. The difference between the lens equation and sum of the basis functions (standard deviation, etc.) can be evaluated to check for cusps. Cusps are small deviations with sharp transitions typically occurring at an integer multiple of the spot size. The cusps tend to be "stiff" equations and are difficult to eliminate later. Cusps tend to be localized, occurring within 20 or so coordinate points. A moving average and standard deviation "window" of about 20 points can be done to test for cusps. Note that the effects near the edge of the ablation will typically have a large standard deviation. If the deviation due to cusps is too large, different fitting parameters can be used to re-evaluate the closeness of the fit. The results should be checked for negative coefficients and their magnitude. Another fit with a different set of rings (usually a smaller number but may be a larger number) will need to be done if zeroing out the negative coefficients causes a large $\chi^2$. For small values, it suffices to set the negative coefficients to zero and re-evaluate $\chi^2$ and check the lens equation versus the solution.

Step 7. Iterate for best solution. If there are 2 cusps (criteria to be determined) or if $\chi^2$ is too large (>100 for the initial settings of 0.25 and 1.0), or if the solution is not close to the lens equation (to be determined), refitting is performed using different fit parameters:

(A) Begin with the number of basis functions, searching from 17–57 at the initial spot size (2 mm);

(B) Next search with a different spot size (1.75 mm, 1.5 mm) and repeat (A);

(C) Next search with extended zone and treatment size such that the sum of extended zone and treatment dimensions is a constant (i.e., 6.2 mm) in 0.05 mm increments, and repeat (A) and (B); and (D) Next search with different $\sigma_j$'s. This can get rather complicated. In one calculation, the initial 200 $\sigma_j$'s were 0.25, and the final 100 $\sigma_j$'s were 1.00. The initial 200 $\sigma_j$'s were changed to 0.5 and (A), (B), and (C) were repeated. Then the 200 $\sigma_j$'s were changed to 199 and (A), (B), and (C) were repeated, and so on.

Step 8. Determine actual pulse locations. The coefficients ai returned from the fit (matrix A) are used to calculate the number of pulses at each radial position for a ring pattern or each lateral position for a strip pattern (i.e., basis functions), $$n_k = a_k/(\text{depth per pulse})$$

With the present fitting routine, if the coefficient is less than zero, it is typically set to zero. For myopia, the coefficients are rarely zero.

For a ring pattern, the pulses are spaced evenly along the circumference, but with a random angle added to the first pulse. Dividing this number into $2\pi$ will give the angular spacing between each pulse. The first pulse of each ring is desirably randomized to avoid a pattern effect.

Step 9. Randomize table. All pulses are grouped into one and randomized before treatment to avoid sequentially generating spatially adjacent treatment pulses.

Geometrical considerations can be addressed during the fitting process for a ring pattern (as in myopia or hyperopia) or after the fitting process for a straight pattern (as in myopic and hyperopic cylinders). For reference, the equation for the treatment space profile for the ring pattern in the fitting step is repeated here:

$$a_i \theta_i(x_j) = a_i \cos^{-1}\left(\frac{x_{0i}^2 + x_j^2 - (spotsize/2)^2}{2 \cdot x_{0i} \cdot x_j}\right)$$

The $a_i$'s are the basis function amplitudes returned by the fitting function (step 7). Each amplitude represents the height of a "ring". The length of the ring is $2\pi x_{0i}$, giving the total number of pulses as for the ring as follow:

$$\text{total pulses} = \frac{2\pi x_{0i}}{\text{spot size}} \cdot \frac{a_i}{\text{depth per pulse}}$$

Because the basis functions have radial dependencies, it is easier to implement the normalization factor during the fit by using the normalized basis functions in the fitting step (step 5) as follows:

$$\bar{a}_i \bar{\theta}_i(x_j) = \frac{\bar{a}_i}{\pi} \theta_i(x_j) = \frac{\bar{a}_i}{\pi} \cos^{-1}\left(\frac{x_{0i}^2 + x_j^2 - (\text{spot size}/2)^2}{\text{spot size} \cdot x_j}\right)$$

The $\vec{a}_i$'s returned from these basis functions are normalized. The total number of pulses per ring is $$\text{total pulses} = \frac{\bar{a}_i}{\text{depth per pulse}}$$

The pulses are spread evenly along the $2\pi$ arc. According to a specific embodiment of randomizing the pulses for treatment in step 9, random phases are added to the starting points (the first pulse per radii). The random phases will reduce the periodicity caused by the "finiteness" of the pulse number.

2. Simulated Annealing Approach

The steps for implementing the method of generating scanning locations and ablation depths utilizing the simulated annealing approach may be analogous to those for the method that employs the least square fitting approach using analytical lens equations.

Step 1. Provide target profile matrix. The target profile matrix contains data that may represent any arbitrary target profile, or may be obtained by evaluating the lens equation at discrete points.

Step 2. Define the basis function in the form of treatment matrix. The treatment matrix contains data that represent ablation profiles (i.e., sizes and shapes). The ablation profiles can be arbitrary as long as they can be measured.

Step 3. Define the positions for evaluations. The positions for evaluations may be selected, for instance, based on the target profile, the ablation profiles, or the like.

Step 4. Define the merit function. Any desirable merit function may be specified. An example is a weighted least square fit with a standard deviation $\sigma_i$ specified for each data point.

Step 5. Apply simulated annealing. The simulated annealing process as illustrated in FIG. 7 and described above is applied to fit the treatment matrix to the target profile matrix to solve for the treatment plan or table containing the amplitudes for a treatment pattern which is in general a two-dimensional pattern.

Step 6. Evaluate closeness of fit. The closeness of the fit is monitored by evaluating the merit function which can be a least square fit error function or any arbitrary function specified by the user. The evaluation occurs in step 26 in the flow chart shown in FIG. 7.

Step 7. Iterate for best solution. As illustrated in FIG. 7, the iteration scheme involves random variation of the PIV and evaluation of the merit function (steps 24-30), and adjusting the "temperature", i.e., the size of incremental change to an element of the PIV (steps 32 and 34).

Step 8. Determine actual pulse locations. The treatment plan or table obtained by solving the target profile fitting equation includes amplitudes of the pulses which, in conjunction with the treatment matrix, provides instructions to the laser to direct pulses with the sizes and depths at the desired locations to achieve the best fit to the target profile.

Step 9. Randomize table. The pulses are randomized for treatment to reduce the periodicity caused by the finiteness of the pulse number.

II. EXEMPLARY SCANNING SYSTEM

Figure 8A:
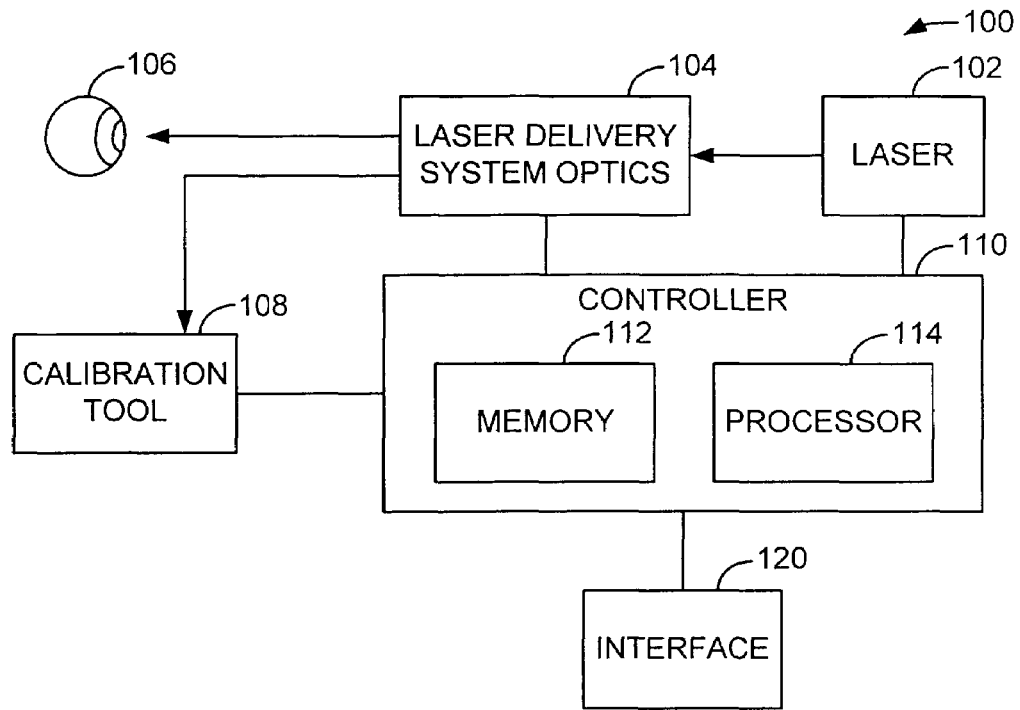
FIG. 8A is a block diagram of the laser system illustrating an embodiment of the present invention.

FIG. 8A shows a block diagram of a scanning system 100 for implementing the method of the present invention to perform corneal sculpting. The scanning system 100 includes a laser 102 for generating a laser beam and laser delivery system optics 104 for delivering the laser beam to a target which is the cornea 106 of an eye. The laser delivery system optics 104 include various optical elements used to focus, modify, and direct the beam in a scanning mode to the cornea 106. The energy level of the laser beam is typically about 50–250 mJ/pulse. Commercially available systems having suitable laser and optics for scanning include, for example, the VISX TWENTY/TWENTY EXCIMER LASER SYSTEM, from VISX, Incorporated of Santa Clara, Calif.; Lasersight, Orlando, Fla.; Chiron Technolas, Germany; and Autonomous Technology, Orlando, Fla.

Optionally, the system 100 may include a calibration tool 108 for determining the characteristics of the laser beam which can be used as feedback for calibrating the scanning system 100. In one embodiment, the calibration tool 108 includes a reference-edge and a photodetector. The calibration tool 108 is placed at a target location for sensing a laser beam directed onto the tool 108. The laser beam can be repeatedly re-directed between the tool 108 and the patient's cornea 106. As such, after determining the size, shape, and/or position of the beam using the tool 108, the laser beam can be applied at a known location on the cornea. A repetitive measurement of intensity and shape characteristics of the laser beam can be made, and a repetitive recalibration of the targeting of the laser beam can be achieved to ensure precise positional accuracy when ablating the cornea 106. Using the sensed information from the calibration tool 108, an algorithm for calculating the locations and number of scanning spots (such as that according to the present invention) can be revised, thereby increasing the accuracy of the sculpting procedure. This calibration information can be used to adjust the ablation algorithm immediately before and/or during each ablation procedure in real time. A more thorough discussion of the calibration procedure is found in commonly assigned U.S. Patent Application entitled "Method and Apparatus for Determining Characteristics of a Laser Beam Spot," Ser. No. 09/395,809, filed Sep. 14, 1999, which is incorporated herein by reference in its entirety.

The scanning system 100 further includes a controller 110 for controlling operation of the laser 102 and the delivery system optics 104, and all activities of the system 100. In one embodiment, the controller 110 includes a hard disk drive (memory 112), a floppy disk drive, and a processor 114. The controller 110 executes system control software, which is a computer program stored in a computer-readable medium such as the memory 112. The memory 112 is typically a hard disk drive, but may also be other kinds of memory. The computer program includes sets of instructions that dictate, for instance, spot ablation pattern, spot ablation depth, depth per pulse, the energy level, spot size and shape, pulse rate, pulse location, and scanning pattern and sequence. It is understood that other computer programs stored on other memory devices including, for example, a floppy disk or another appropriate drive, may also be used to operate the controller 110.

An interface 120 is provided between a user and the controller 110 typically in the form of a display monitor for displaying information, and an input device such as a keyboard, a mouse, and/or a light pen to allow the user to communicate with the controller 110.

The scanning process can be implemented using a computer program product that is executed by the controller 110. The computer program code may be written in any conventional computer readable programming language. Suitable program code is entered into a single file, or multiple files, using a conventional text editor, and stored or embodied in a computer usable medium, such as a memory system of the computer. If the entered code text is a high level language, the code is compiled, and the resultant compiler code is then linked with an object code of precompiled library routines. To execute the linked, compiled object code, the system user invokes the object code, causing the computer system to load the code in memory. The processor 114 then reads and executes the code to perform the tasks identified in the program.

Figure 8B:
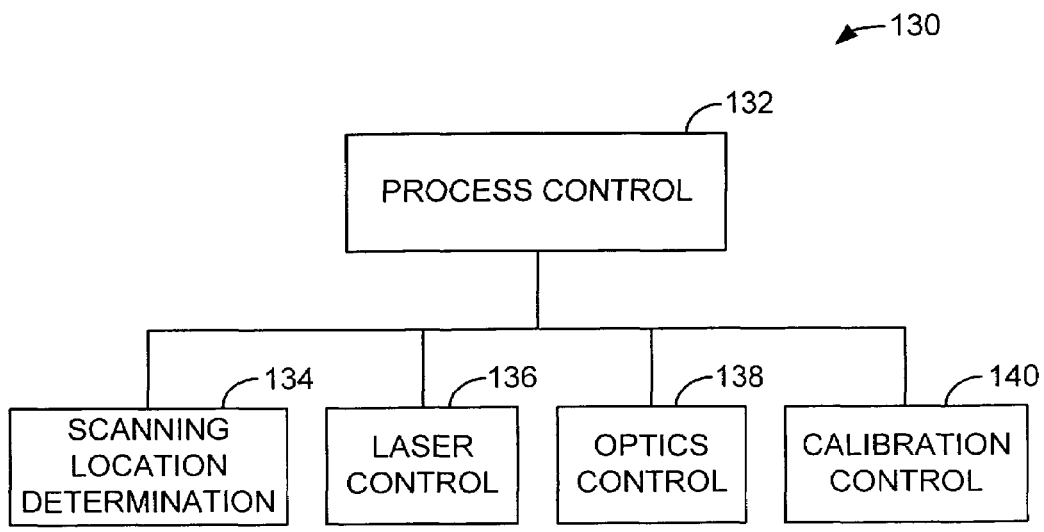
FIG. 8B is a block diagram of the control structure of a computer program according to a specific embodiment.

FIG. 8B shows an illustrative block diagram of the control structure of the system control software, computer program 130, according to a specific embodiment. Through the input device of the interface 120, a user enters a set of process parameters into a process control subroutine 132 in response to menus or screens displayed on the monitor. The process parameters include input data needed to operate the system 100 including, for example, the laser beam energy and spot size, and all the input necessary to determine the pulse locations and numbers according to the algorithm described above.

A scanning location determination subroutine 134 includes program code for accepting the process parameters from the process control subroutine 132, and for determining the scanning pulse locations and numbers according to the algorithm described above. The scanning location determination subroutine 134 produces laser control parameters and optics control parameters used in operating the laser 102 and delivery system optics 104. A laser control subroutine 136 includes program code for accepting laser control parameters to control operation of the laser 102. An optics control subroutine 138 includes program code for accepting optics control parameters to control operation of the system optics 104. A calibration control subroutine 140 includes program code for controlling the calibration tool 108 to determine the characteristics of the laser beam generated by the system 100 and to provide feedback data to calibrate the laser 102 and delivery system optics 104 for improved scanning accuracy and precision. The calibration data can also be used to adjust the ablation algorithm in the scanning location determination subroutine 134 to revise the calculation of scanning spot locations and numbers.

The computer program 130 can be used to determine the pulse locations and numbers, and to calibrate the laser system 100 in real time. In this way, the target profile for a patient can be entered just prior to performing the corneal sculpting procedure.

III. EXAMPLES

The following experimental examples are used to illustrate the methods of the present invention.

A. Least Square Fitting Approach Using Analytical Lens Equation

The examples were undertaken using a scanning laser system having a Questek impulse excimer with a pre-objective galvo scanner. The pulse rate was 70 Hz. The treatment time is dependent on the amount of tissue removed per pulse (or tissue removed per second). For instance, a 6 mm spot will remove 9 times more material per pulse than a 2 mm spot. To keep the ablation rate constant, the 2 mm spot will need to increase the repetition rate by 9 as compared to the 6 mm spot. Decreasing the spot further will increase the number of pulses dramatically, as illustrated in the following table.

| Spot Size | Volume [mm$^3$] |
|---|---|
| 0.5 mm | $4.7 \times 10^{-9}$ |
| 1.0 mm | $1.9 \times 10^{-8}$ |
| 2.0 mm | $7.5 \times 10^{-8}$ |
| 6.0 mm | $6.8 \cdot 10^{-7}$ |

1. Myopia

Figure 9:
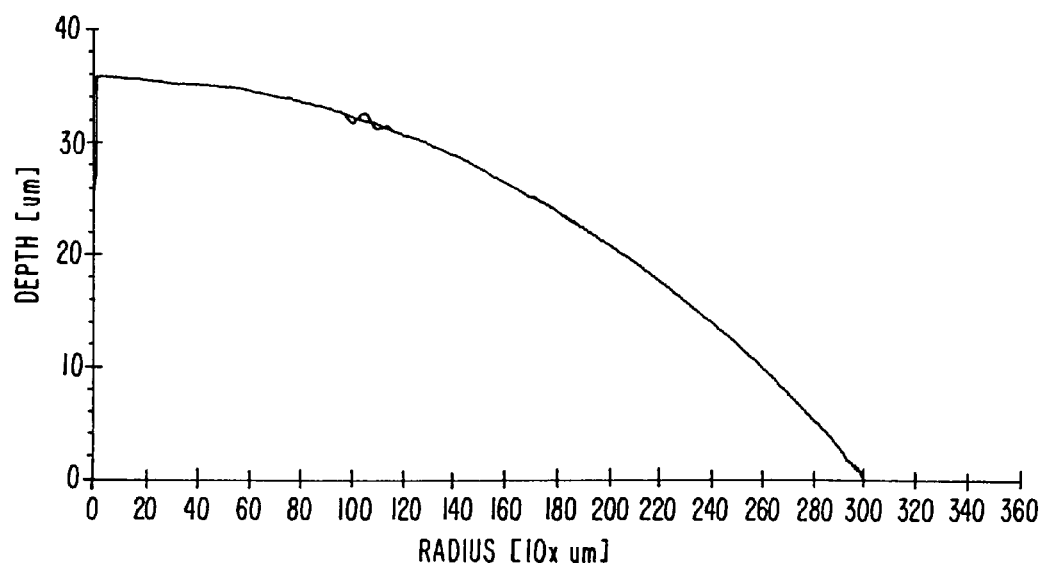
FIG. 9 shows the result of fitting a myopic lens equation using 27 equally spaced basis functions.

FIG. 9 is a graph comparing a fit using the method of the present invention to the theoretical lens equation. The number of basis, M, used in the fit is 27. The fit is given a standard deviation, $\sigma=0.25$, for the first 150 points and a value four times larger for the last 150 points, $\sigma=1.0$. Having $\sigma$ smaller for the inner portion of the curve gives the central 3 mm of a 6 mm ablation more importance than the outer portion. The difference in the quality of fit between the inner and the outer portions is evident, where the fit is much better in the inner portion. The outer portion shows a slight departure.

One gross feature observed in this fit is the "bump" at the one-millimeter distance. This occurs because of the size of the spot (2 mm) is an integral multiple of the ablation zone (6 mm). One way to fix the problem is to increase the ablation zone slightly such that the ablation zone is not an integer multiple of the spot. This will also taper the outer perimeter giving a smooth transition from the ablated area to the non-ablated area. Further, there are numerous small bumps near the center ablation zone in FIG. 9. These manifest themselves as concentric rings when the ablations are tested on plastics. Increasing the number of basis functions will eliminate most of the rings.

Figure 10:
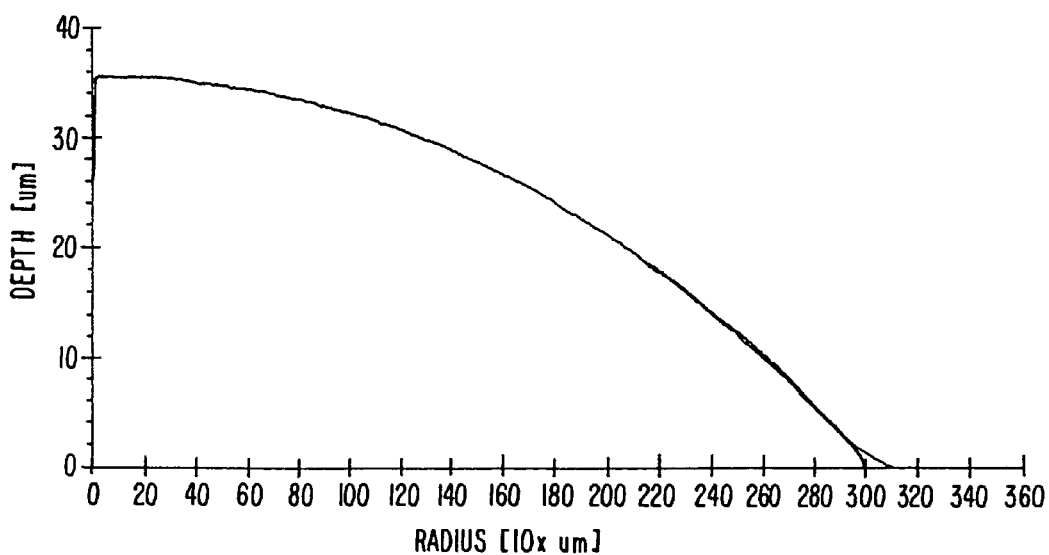
FIG. 10 shows the result of an extended zone fit of a myopic lens equation with 47 equally spaced basis functions.

Shown in FIG. 10 is the same fit but with an increase from 27 to 47 basis functions. The ablation zone is not an integer multiple of the spot. The fit has the extended smooth transition between the ablated and non-ablated zones. Most of the undulations have disappeared. It should be noted, however, that care needs to be taken when increasing the number of basis functions, because too many basis function may cause the solution to require negative values making such solutions not physically obtainable.

Figure 11:
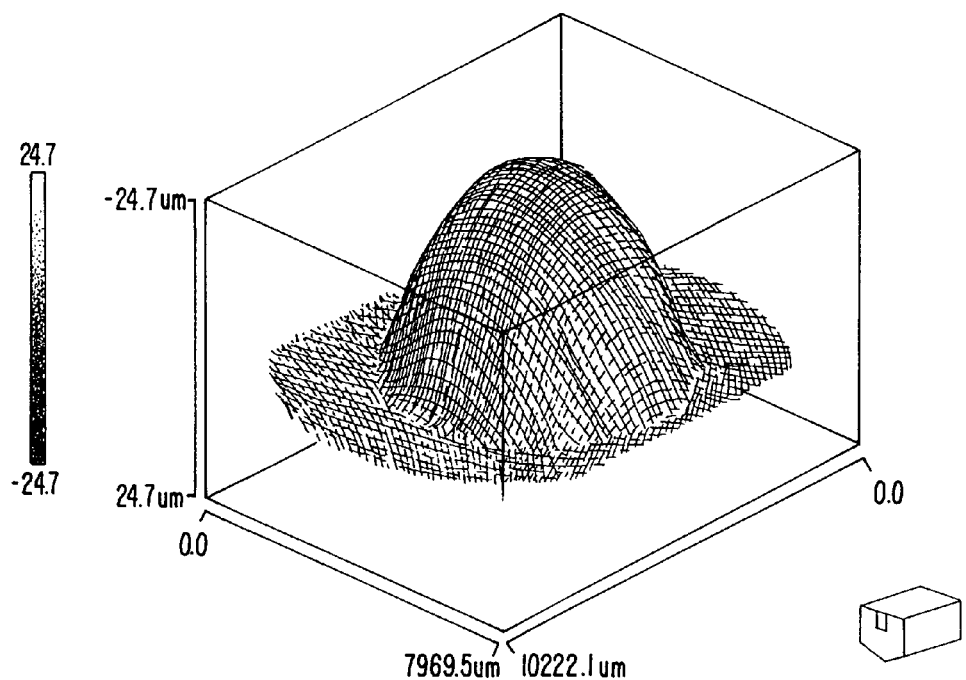
FIG. 11 is an interferometer image of a −4 diopter myopic lens ablation profile using the simulation output from FIG. 10.

FIG. 11 is an interferometer image of a −4 diopter ablation on a plastic using the simulation output from FIG. 10 (extended fit with 47 basis functions) and a spot size of approximately 2.1 mm. The salient feature is the circular over-ablation at 1 mm radius.

Figure 12:
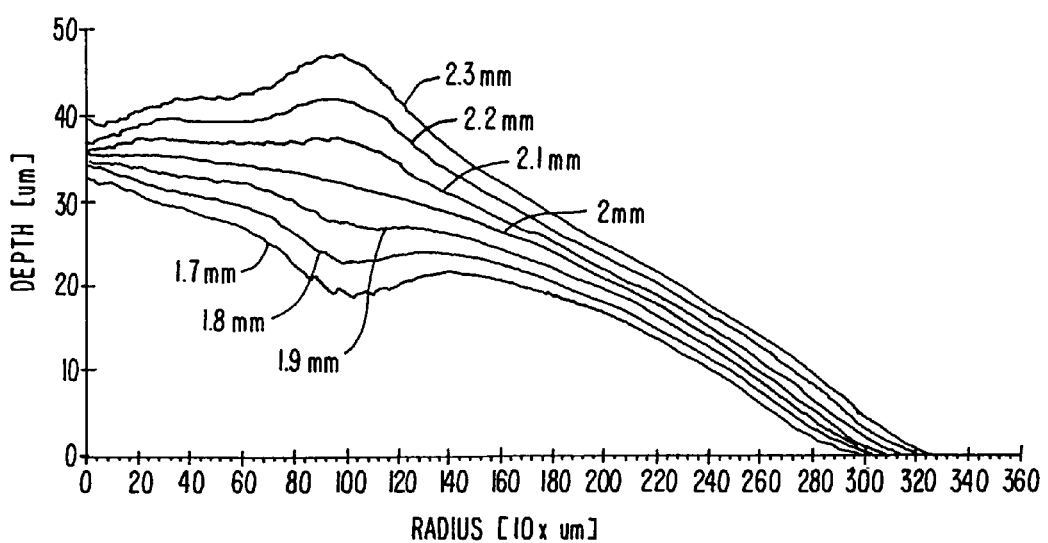
FIG. 12 shows ablation profile changes due to spot size variations.

FIG. 12 shows the characteristics of the simulated ablation profiles of a −4 diopter ablation with 47 basis functions with variations in spot sizes from a 2 mm reference spot size. The curves above the 2 mm reference curve have 5, 10, 15 percent larger spot sizes (i.e., 2.1 mm, 2.2 mm, and 2.3 mm), while the curves below have 5, 10, 15 percent smaller spot sizes (i.e., 1.9 mm, 1.8 mm, and 1.7 mm). The dip or peak at 1 mm becomes larger as the spot size deviates from nominal, and the under- or over-ablation is non-linear. As a result, a change in spot size may remove less or more material and change the overall profile.

2. Hyperopia

Figure 13:
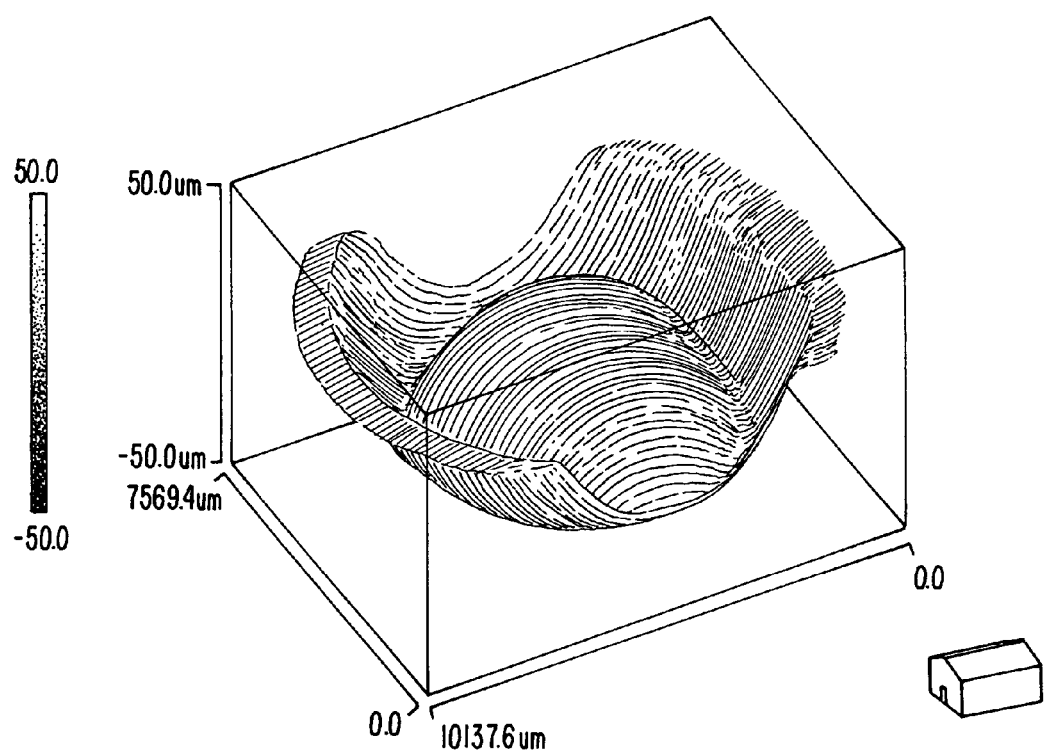
FIG. 13 is an interferometer image of a hyperopic lens ablation profile.

FIG. 13 is an interferometer image of a hyperopic ablation profile of a +4 diopter ablation with 33 basis functions using a 2 mm spot size for a 6 mm ×9.6 mm ablation zone. The method to generate hyperopic lenses is similar to that for myopia. The fitting requirement for hyperopia is less restrictive than for myopia. In myopia, both the ablation's central and perimeter contours (and everything in between) desirably follow the lens equation. In hyperopia, the ablation is a negative lens, so that the central portion has very few pulses and the perimeter has the majority of the pulses. The fitting in the central portion is much less stringent for hyperopia than for myopia. The pulses desirably are able to extend beyond the 6 mm treatment zone length in hyperopia. The outermost pulses have their centers at the 3 mm radius. For a 2 mm spot, it is desirable for the pulse to extend beyond the 3 mm radius going to about 3.5 mm to achieve a good fit. This extension produces an overall ablation diameter of about 9.6 mm. To reduce the ablation size, a smaller spot may be used.

Figure 14A:
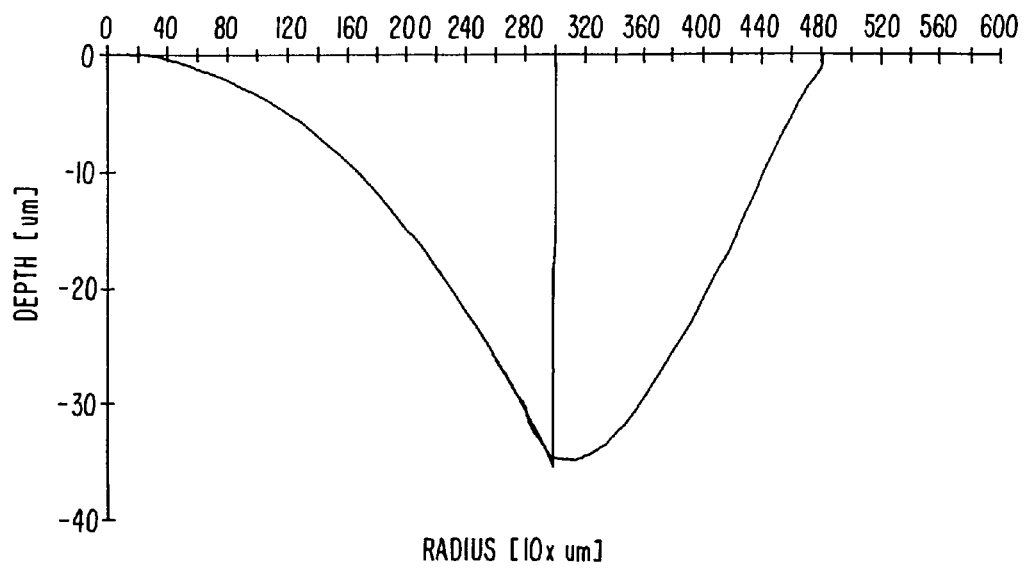
FIGS. 14A and 14B show extended hyperopic lens fit with two different spot sizes.
Figure 14B:
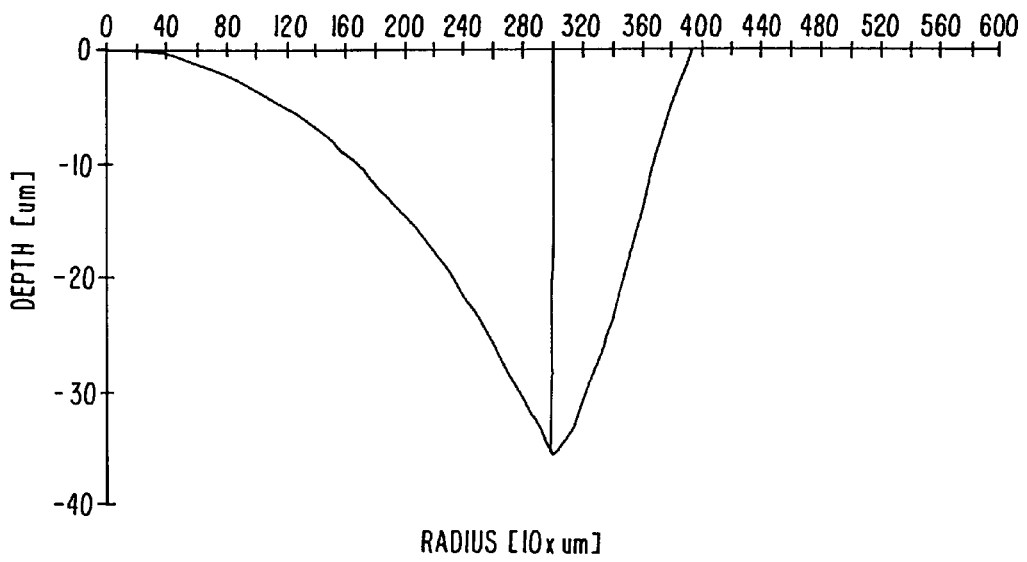

FIGS. 14A and 14B are graphs of two hyperopic lenses employing the same basis functions used in the myopia examples and two different spot sizes. FIG. 14A uses a 2 mm spot and FIG. 14B uses a 1.5 mm spot. The effective dimensions are 6×10 and 6×8 mm ablations, respectively. A transition zone is observed from the 3 mm radius onwards. The spot size has a large influence on this transition zone. The larger the spot size, the larger the transition zone becomes. For a 6 mm optical zone, a 2 mm spot produces a transition zone of 4.8 mm radius, while a 1.5 mm spot produces a transition zone of 3.9 mm radius.

Fits to a hyperopic lens produce different characteristics from those obtained from the myopic fits. The hyperopic fits are relatively simple because the perimeters are allowed to "float" thereby producing a transition zone. As with myopia, an extended zone is desirable for the hyperopic fit. This extended zone is about 0.8 times the radius. This places the spots at 3.8 mm for a 2 mm spot. Adding the radius of the 2 mm spot gives the ablation zone radius of 4.8 mm.

$$\frac{\text{treatment zone}}{\text{radius}} = \text{optical zone} + 1.8 \, (\text{spot size}/2)$$

Based on this equation, the treatment zone diameter for a 1.5 mm spot is 8.7 mm.

3. Hyperopic Cylinder

Figure 15:
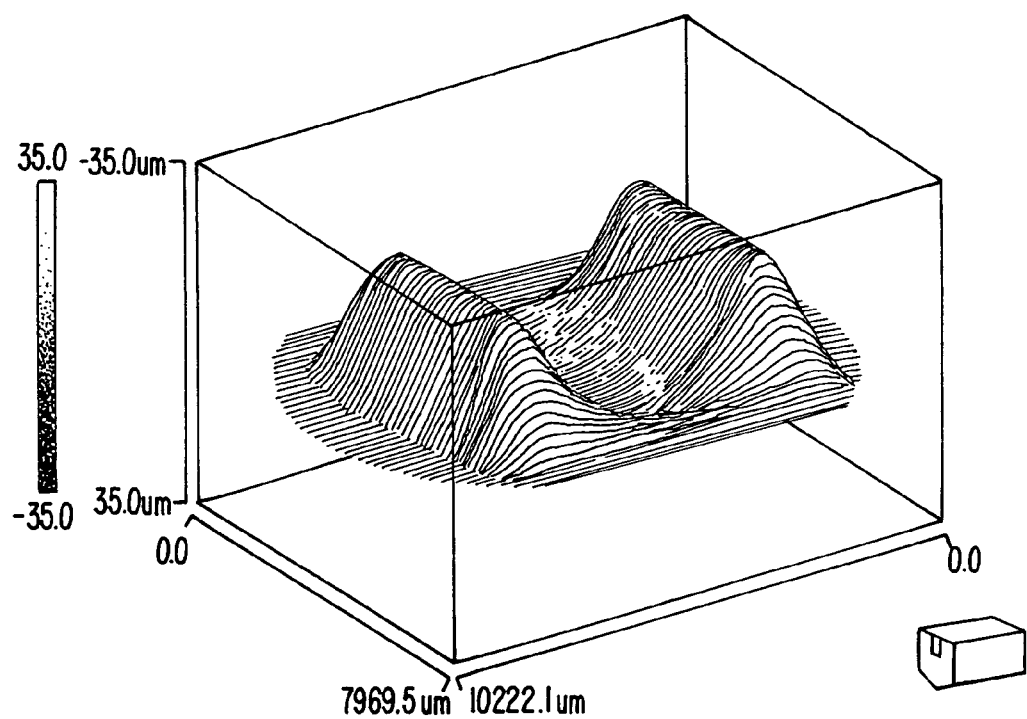
FIG. 15 is an interferometer image of a −4D hyperopic cylinder ablation profile.

Using the appropriate lens equation and basis functions, a hyperopic cylinder ablation profile is generated for a +4 diopter ablation with 33 basis functions using a 2 mm spot size for a 6 mm×9.6 mm ablation zone, as shown in FIG. 15.

Employing the method of the invention, the fit returns the amplitudes of the basis functions. Stacking the pulses vertically will give the correct depth but it will not produce the lateral dimensions needed. As described earlier, offsetting the pulses will produce the trench. The boundary conditions are given by the rectangular perimeter of the hyperopic cylinder. For example, a 5×9 mm hyperopic cylinder has a 9 mm width along the lens direction (similar to plain hyperopia) and has a 5 mm cut along the perpendicular directions. The 5 mm is the length of the trench not including the transition zone. The transition zone is the overlap-offset used to generate the basis "trenches." The slop of the transition zone is given by $$\text{slope} = \frac{\text{depth per pulse}}{\text{offset}}$$

The offset is constrained by the total depth, the spot size, and trench length. The relationship among the total depth, spot size, and offset is given by $$\text{step size} = \frac{\text{spot size}}{\text{depth/depth per pulse}}$$

The transition zone is one spot size in width. The number of the total pulses for this basis trench is not simply the depth/depth per pulse, since it also depends on the trench length. Instead, the number of pulses is $$\text{no. of pulses} = \frac{\text{length of trench}}{\text{spotsize}} * \frac{\text{depth}}{\text{depth per pulse}}$$

For myopia and hyperopia, the periodicity is reduced considerably by adding a random starting phase to each ring. This approach is not available to ablation profiles with cylindrical symmetry such as hyperopic and myopic cylinders. Starting the trench with a repetitious position will produce a deeper pattern at that position with a feathering effect at the ending positions. The feathering effect occurs because the number of pulses per basis is different making the offsets different. A very small random phase or position is desirably added to reduce the periodicity of the scans. For instance, a small random edges position is added to the locations to blend the spot.

Generating a myopic cylinder ablation profile is similar to generating a hyperopic cylinder profile. The lens equations are different but the same basis functions are used. Fitting the basis functions to the lens equation for a myopic cylinder is more stringent than for a hyperopic cylinder, however, because the fit is preferably good from the center to the perimeter with a small allowance for the transition zone. The fit in the center region for a hyperopic cylinder is less rigorous.

In addition, care needs to be taken when the treatment ring approaches the origin. Analytically, the basis functions for the myopic cylinder are equivalent to the ones used for hyperopic cylinder. The difference is the hyperopic cylinder treatment does not approach the origin. At the origin, the basis functions overlap on themselves. The overlap is $$y_i(x) = \sqrt{(\text{spot size}/2)^2 - (x - x_{0i})^2} + \sqrt{(\text{spot size}/2)^2 - (x + x_{0i})^2}$$

where spot size/$2<(x_{0i}+x)$. This "overlap" is part of the algorithm and is used if the fit goes from 0 to the treatment zone radius, to account for the situation where the spot passes through the original ([0]).

B. Simulated Annealing Approach

An example employs the simulated annealing approach for fitting the ablation of a −2 diopter elliptical profile which has a major axis length of 16 mm and a minor axis length of 12 mm, and a maximum depth of about 31 μm. Due to the bilateral symmetry, only one quarter of the surface is used in the fitting calculations. Any overlaps caused by large pulses near the axes of symmetry are reflected back relative to the axes of symmetry to ensure that the calculations are correct. The pulse shapes are circular having diameters of 5.5 mm, 5 mm, 4 mm, 3 mm, 2 mm, and 1 mm at evenly spaced (100 μm) intervals. There are about 2000 total pulse basis functions. The merit function in this case is the root mean square error between the target shape and the current solution.

Figure 16A:
FIGS. 16a–16c are graphs illustrating the results of the simulated annealing process at different stages of the iteration for fitting an elliptical profile.
Figure 16B:
Figure 16C:
Figure 17A:
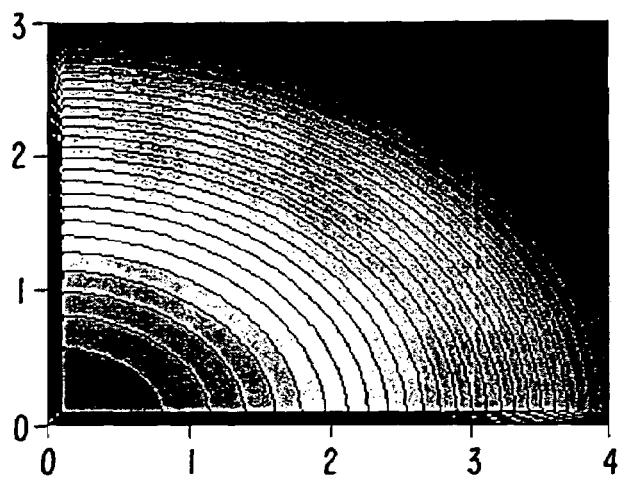
FIGS. 17a and 17b show contour plots of the elliptical target profile and the calculated profile.
Figure 17B:
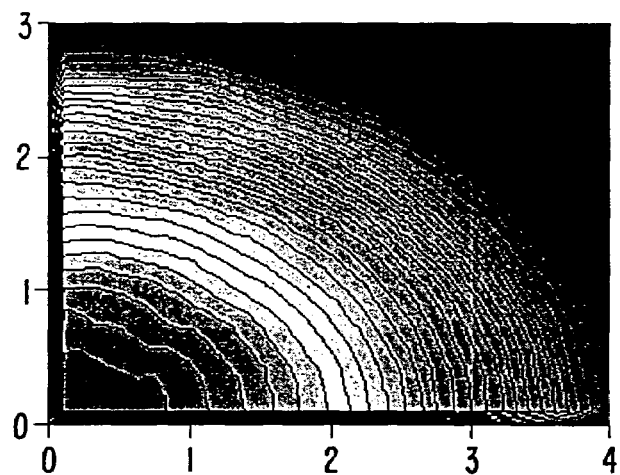
Figure 18:
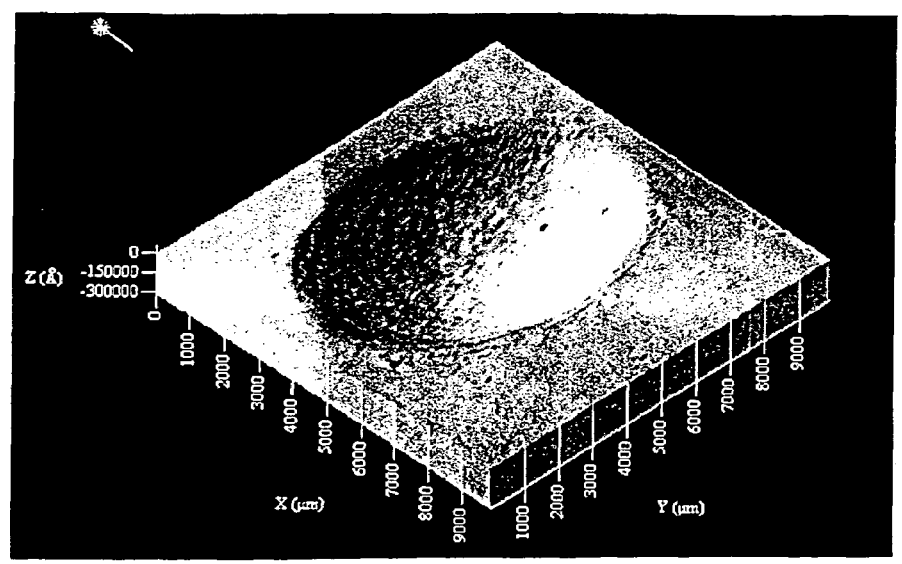
FIG. 18 shows a −4 diopter elliptical ablation profile based on the solution obtained from the simulated annealing process of FIGS. 16a–16c.

FIGS. 16a–16c show the simulated annealing process at different stages of the iteration to achieve the best fit. Each figure shows (1) a working solution obtained from the current best guess of the treatment plan or table, (2) the target profile, and (3) delta representing the difference between the working solution and the target profile. At the initial guess with zero iteration shown in FIG. 16a, the errors are quite large. The errors are reduced to about 2 μm or less after 10,000 iterations as shown in FIG. 16b. At 1,000,000 iterations in FIG. 16c, the errors are less than 1 μm and well distributed over the surface. The contour plots of the target profile and the calculated profile are illustrated in FIGS. 17a and 17b, respectively. About 50% of the calculated profile falls within 0.1 μm of the target profile, and about 80% of the calculated profile falls within 0.25 μm of the target profile. The solution is used by a Tencor scanner to produce the ablation profile shown in FIG. 18.

It is to be understood that the above description is intended to be illustrative and not restrictive. Many embodiments will be apparent to those of skill in the art upon reviewing the above description. For instance, some of the above equations are developed using a fixed spot shape and size. In alternate embodiments, the spot shape and/or spot size may be varied. Variation of spot size and shape is described, for instance, in commonly assigned European Patent No. 0628298 for "METHOD AND SYSTEM FOR LASER TREATMENT OF REFRACTIVE ERRORS USING OFFSET IMAGING", filed May 5, 1994 (Application No. 94303256.5) and issued Apr. 1, 1998, which is incorporated herein by reference in its entirety. Different merit functions can be prescribed. Other numerical approaches may be used to solve the target profile fitting equation. The desired lens profile may be an elliptical profile, a hyperopic elliptical profile, a myopic elliptical profile, a circular profile, a linear profile, an asymmetric profile, or an arbitrary two-dimensional lens profile. The scope of the invention should, therefore, be determined not with reference to the above description, but instead should be determined with reference to the appended claims along with their full scope of equivalents.

What is claimed is:

1. A method for fitting a three-dimensional target profile, the method comprising:
   providing a two-dimensional user-specified basis function including overlapping portions that are disposed at a plurality of locations and overlap with one another to represent a three-dimensional profile which has symmetry with respect to a two-dimensional section extending along a treatment pattern; and
   fitting the three-dimensional target profile with the two-dimensional user-specified basis function to obtain a distribution of the overlapping portions that are disposed at the plurality of locations, each overlapping portion representing a two-dimensional treatment portion to be applied to a tissue and combined with other overlapping portions to achieve the three-dimensional target profile for treatment of the tissue according to the distribution obtained from the fitting.

2. The method of claim 1 wherein the three-dimensional profile has symmetry with respect to a two-dimensional section oriented radially from an axis of symmetry and extending in a generally circular treatment pattern around the axis.

3. The method of claim 1 wherein the three-dimensional profile has symmetry with respect to a two-dimensional section oriented normal across a generally straight treatment pattern.

4. The method of claim 1 wherein the basis function includes M discrete basis functions representing M overlapping portions.

5. A method for fitting a three-dimensional target profile, the method comprising:
   providing a two-dimensional basis function including overlapping portions to represent a three-dimensional profile which has symmetry with respect to a two-dimensional section extending along a treatment pattern; and
   fitting the three-dimensional target profile with the two-dimensional basis function to obtain a distribution of the overlapping portions;
   wherein the three-dimensional profile has symmetry with respect to a two-dimensional section oriented radially from an axis of symmetry and extending in a generally circular treatment pattern around the axis;

wherein the overlapping portions are generally circular, and the two-dimensional basis function comprises discrete basis functions each representing a coverage angle of one of the overlapping portions as a function of a distance from the axis of symmetry.

6. A method for fitting a three-dimensional target profile, the method comprising:

providing a two-dimensional basis function including overlapping portions to represent a three-dimensional profile which has symmetry with respect to a two-dimensional section extending along a treatment pattern; and fitting the three-dimensional target profile with the two-dimensional basis function to obtain a distribution of the overlapping portions;

wherein the three-dimensional profile has symmetry with respect to a two-dimensional section oriented normal across a generally straight treatment pattern;

wherein the overlapping portions are generally circular, and the two-dimensional basis function comprises discrete basis functions each representing a depth of one of the overlapping portions as a function of a distance from the axis of symmetry.

7. A method for fitting a three-dimensional target profile, the method comprising:

providing a two-dimensional basis function including overlapping portions to represent a three-dimensional profile which has symmetry with respect to a two-dimensional section extending along a treatment pattern; and fitting the three-dimensional target profile with the two-dimensional basis function to obtain a distribution of the overlapping portions;

wherein the basis function includes M discrete basis functions representing M overlapping portions;

wherein the M discrete basis functions represent M overlapping portions across a treatment zone length representing the length across a generally two-dimensional section which is oriented normal across a generally straight treatment pattern or which is oriented radially across a generally circular treatment pattern.

8. The method of claim 7 wherein the overlapping portions are generally circular and have a generally uniform energy profile.

9. The method of claim 8 wherein (A) for a treatment profile having a generally uniform two-dimensional section oriented normal across a generally straight treatment pattern, the discrete basis functions represent the two-dimensional section as $$X_i(x_j) = y_i(x_j) = \sqrt{(s/2)^2 - (x_j - x_{0i})^2} \text{ or}$$

(B) for a treatment profile having a generally uniform two-dimensional section oriented radially across a generally circular treatment pattern, the discrete basis functions represent the two-dimensional section as $$X_i(x_j) = \theta_i(x_j) = \cos^{-1}\left(\frac{x_j^2 + x_{0i}^2 - (s/2)^2}{2 \cdot x_{0i} \cdot x_j}\right)$$

where
s is the diameter of the overlapping portion;
j=1, ..., N;

$x_j$ is a reference x-coordinate for the two-dimensional section measured from an optical axis of the cornea of a $j^{th}$ evaluation point for the center of the overlapping portion;

$x_{0i}$ is an x-coordinate for a center of an $i^{th}$ overlapping portion;

$(x_{0i}-s/2) \leq x_j < (x_{0i}+s/2)$;

$y_i(x_j)$ is a depth of the $i^{th}$ basis function for the generally straight treatment pattern; and $\theta_i(x_j)$ is a coverage angle of the $i^{th}$ basis function for the generally circular treatment pattern.

10. The method of claim 9 wherein $x_{0i}$ is specified for M number of equally spaced overlapping portions as $x_{0i}=i*[(L-s+e)/M]$, where
L is the treatment zone length;
e is an extended zone; and
i=1, ..., M.

11. The method of claim 10 wherein e is set to about 0.1 to about 0.5 mm.

12. A method for fitting a three-dimensional target profile, the method comprising:

providing a two-dimensional basis function including overlapping portions to represent a three-dimensional profile which has symmetry with respect to a two-dimensional section extending along a treatment pattern; and fitting the three-dimensional target profile with the two-dimensional basis function to obtain a distribution of the overlapping portions;

wherein the basis function includes M discrete basis functions representing M overlapping portions;

wherein M is equal to about 7 to about 97.

13. A method for fitting a three-dimensional target profile, the method comprising:

providing a two-dimensional basis function including overlapping portions to represent a three-dimensional profile which has symmetry with respect to a two-dimensional section extending along a treatment pattern;

fitting the three-dimensional target profile with the two-dimensional basis function to obtain a distribution of the overlapping portions, wherein the basis function includes M discrete basis functions representing M overlapping portions; and refitting the target function with the basis function by varying the number of overlapping portions M to iterate for a best fit.

14. A method for fitting a three-dimensional target profile, the method comprising:

providing a two-dimensional basis function including overlapping portions to represent a three-dimensional profile which has symmetry with respect to a two-dimensional section extending along a treatment pattern; and fitting the three-dimensional target profile with the two-dimensional basis function to obtain a distribution of the overlapping portions;

wherein the target function is:

(A) for myopia and myopic cylinder, $$f(x_j) = \sqrt{R_1^2 - x_j^2} - \sqrt{\left(\frac{R_1(n-1)}{n-1+R_1 D}\right) - x_j^2} + C \text{ or}$$

(B) for hyperopia and hyperopic cylinder, $$f(x_j) = R_1 - \frac{R_1(n-1)}{n-1+R_1D} - \sqrt{R_1^2 - x_j^2} + \sqrt{\left(\frac{R_1(n-1)}{n-1+R_1D}\right) - x_j^2} \quad \text{or}$$

(C) for phototherapeutic keratectomy, $$f(x_j) = d;$$

where $$0 \leq x_j \leq (L-\text{shift});$$

j=0, 1, . . . , N−1;

$$C = \sqrt{R_1^2 - s^2/4} + \sqrt{\left(\frac{R_1(n-1)}{n-1+R_1D}\right) - \frac{s^2}{4}};$$

$x_j$ is an x-coordinate measured from an optical axis of the cornea of the $j^{th}$ evaluation point for the center of the overlapping portion;
s is the diameter of the overlapping portion;
$R_1$ is the anterior radius of curvature of the cornea in meters;
$R_2$ is the final anterior radius of curvature of the cornea in meters;
n =1.377 is the index of refraction of the cornea;
D is the lens power of the overlapping portion in diopters;
L is the treatment zone length representing the length across a generally uniform section which is oriented normal across a generally straight treatment pattern for myopic or hyperopic cylinders, or which is oriented radially across a generally circular treatment pattern for myopia or hyperopia;
shift is the amount of emphasis shift; and
d is a constant depth.

15. The method of claim 14 wherein the shift is about 0 to about 0.2.

16. The method of claim 14 wherein $x_j=j*[(L-\text{shift})/N]$.

17. The method of claim 14 wherein the basis function includes M discrete basis functions representing M overlapping portions, and wherein fitting the target function with the basis function comprises solving the following equation for coefficients $a_i$, representing treatment depth for the $i^{th}$ overlapping portion;

$$f(x_j) = \sum_{i=1}^{M} a_i X_i(x_j)$$

where
$X_i(x_j)$ is the $i^{th}$ basis function; and
i=1, . . . , M.

18. A method for fitting a three-dimensional target profile, the method comprising:
providing a two-dimensional basis function including overlapping portions to represent a three-dimensional profile which has symmetry with respect to a two-dimensional section extending along a treatment pattern; and
fitting the three-dimensional target profile with the two-dimensional basis function to obtain a distribution of the overlapping portions;
wherein fitting the target function and the basis function comprises specifying a deviation for each of the N discrete evaluation points.

19. The method of claim 18 further comprising refitting the target function with the basis function by varying the deviations to iterate for a best fit.

20. A method for fitting a three-dimensional target profile, the method comprising:
providing a two-dimensional basis function including overlapping portions to represent a three-dimensional profile which has symmetry with respect to a two-dimensional section extending along a treatment pattern; and
fitting the three-dimensional target profile with the two-dimensional basis function to obtain a distribution of the overlapping portions;
wherein fitting the target function and the basis function comprises evaluating closeness of the fit and repeating the fitting step if the closeness does not fall within a target closeness.

21. A method for fitting a three-dimensional target profile, the method comprising:
providing a two-dimensional basis function including overlapping portions to represent a three-dimensional profile which has symmetry with respect to a two-dimensional section extending along a treatment pattern; and
fitting the three-dimensional target profile with the two-dimensional basis function to obtain a distribution of the overlapping portions;
wherein the target function and the basis function are fitted using a least square fit.

22. A method for fitting a three-dimensional target profile, the method comprising:
providing a two-dimensional basis function including overlapping portions to represent a three-dimensional profile which has symmetry with respect to a two-dimensional section extending along a treatment pattern;
fitting the three-dimensional target profile with the two-dimensional basis function to obtain a distribution of the overlapping portions; and
refitting the target function with the basis function by varying the size of at least one of the overlapping portions to iterate for a best fit.

23. A method for fitting a three-dimensional target profile, the method comprising:
providing a two-dimensional basis function including overlapping portions to represent a three-dimensional profile which has symmetry with respect to a two-dimensional section extending along a treatment pattern; and
fitting the three-dimensional target profile with the two-dimensional basis function to obtain a distribution of the overlapping portions;
wherein the overlapping portions have different sizes.

24. A method for fitting a three-dimensional target profile, the method comprising:
providing a two-dimensional basis function including overlapping portions to represent a three-dimensional profile which has symmetry with respect to a two-dimensional section extending along a treatment pattern; and fitting the three-dimensional target profile with the two-dimensional basis function to obtain a distribution of the overlapping portions;
wherein the target function and the basis function are fitted using a simulated annealing process.

25. A method for fitting a three-dimensional target profile, the method comprising:
providing a two-dimensional basis function including overlapping portions to represent a three-dimensional profile which has symmetry with respect to a two-dimensional section extending along a treatment pattern;
fitting the three-dimensional target profile with the two-dimensional basis function to obtain a distribution of the overlapping portions; and
specifying a merit function representing an error of fit between the target function and the basis function; and minimizing the merit function.

26. A method for fitting a three-dimensional target profile, the method comprising:
providing a two-dimensional basis function including overlapping portions to represent a three-dimensional profile which has symmetry with respect to a two-dimensional section extending along a treatment pattern;
fitting the three-dimensional target profile with the two-dimensional basis function to obtain a distribution of the overlapping portions; and
refitting the target function with the basis function by selecting an overlapping portion location and varying the characteristics of the overlapping portion at the selected location to iterate for a best fit.

* * * * *